US005731182A

United States Patent [19]
Boyce

[11] Patent Number: 5,731,182
[45] Date of Patent: Mar. 24, 1998

[54] NON-MAMMALIAN DNA VIRUS TO EXPRESS AN EXOGENOUS GENE IN A MAMMALIAN CELL

[75] Inventor: Frederick M. Boyce, Belmont, Mass.

[73] Assignee: The General Hospital Corporation, Boston, Mass.

[21] Appl. No.: 486,341

[22] Filed: Jun. 7, 1995

Related U.S. Application Data

[63] Continuation-in-part of Ser. No. 311,157, Sep. 23, 1994.

[51] Int. Cl.$^6$ .............................. C12N 9/00; C12N 15/63; C12P 21/02
[52] U.S. Cl. ................. 435/183; 435/320.1; 435/69.1; 435/70.1
[58] Field of Search ............................ 435/183, 183 T, 435/320.1, 69.1, 70.1

[56] References Cited

U.S. PATENT DOCUMENTS 5,476,781  12/1995  Moyer et al. ................... 435/240.2

FOREIGN PATENT DOCUMENTS

WO 95/23866  9/1995  WIPO.

OTHER PUBLICATIONS

Carbonell L.F. et al.; "Baculovirus–Mediated Expression of Bacterial Genes in Dipteran and Mammalian Cells" Journal of Virology, 56:153–160 (1985).

Carbonell L.F. et al.; "Baculovirus Interaction with Nontarget Organisms:A irus–Borne Reporter Gene Is Not Expressed in Two Mammalian Cell Lines"; Applied and Enviromental Microbiology 56:1412–1417 (1987).

Volkman, et al., "In Vitro Survey of Autographa Californica Nuclear Polyhedrosis Virus Interaction with Nontarget Vetebrate Host Cells", applied and Enviromental Microbiology, 45:1085–1093, 1983.

Brusca et al., "Autographa Californica Nuclear Polyhedrosis Virus Efficiently Enters but Does Not Replicate in Poikilothermic Vertebrate Cells", Intervirology 26:207–222, 1986.

Hoopes et al., "In Vitro Transcription of Baculovirus Immediate Early Genes: Accurate mRNA Initiation By Nuclear Extracts from Both Insect and Human Cells", Proc. Natl. Acad. Sci., 88:4513–4517, 1991.

Huber et al., "Retroviral–mediated Gene Therapy for the Treatment of Hepatocelluar Carcinoma: An Innovative Approach for Cancer Therapy", Proc. Natl. Acad. Sci., 88:8039–8043, 1991.

Patel et al., "A New Method for the Isolation of Recombinant Baculovirus", Nucleic Acids Research, 20:97–104, 1992.

Rana et al., "Cell–Extracellular Matrix Interactions Can Regulate the Switch Between Growth and Differentiation in Rat Hepatocytes . . . ", Molecular and Cellular Biology, 14:5858–5869, 1994.

Tjia et al., "Autographa Californica Nuclear Polyhedrosis Virus (AcNPV) DNA Does Not Persist in Mass Cultures of Mammalian Cells", Virology, 125:107–117, 1983.

Vile et al., "Gene Transfer Technologies for the Gene Therapy of Cancer", Gene Therapy, 1:88–98, 1994.

School of Biological Sciences, Canberra, Australia, 1991.

Boyce, F.M. et al. (1996) "Baculovirus–mediated gene transfer into mammalian cells" Proc. Nat'l. Acad. Sci., USA 93:2348–2352, Mar. 1996.

*Primary Examiner*—Robert A. Wax
*Assistant Examiner*—Kawai Lau
*Attorney, Agent, or Firm*—Fish & Richardson, P.C.

[57] ABSTRACT

Disclosed is a method of expressing an exogenous gene in a mammalian cell, involving infecting the cell with a non-mammalian virus (e.g., a baculovirus) whose genome carries an exogenous gene, and growing the cell under conditions such that the gene is expressed. Also disclosed is a method of treating a gene deficiency disorder in a mammal by providing to a cell a therapeutically effective amount of a virus whose genome carries an exogenous gene and growing the cell under conditions such that the exogenous gene is expressed in the mammal.

39 Claims, 8 Drawing Sheets

FIG. 6A
FIG. 6B
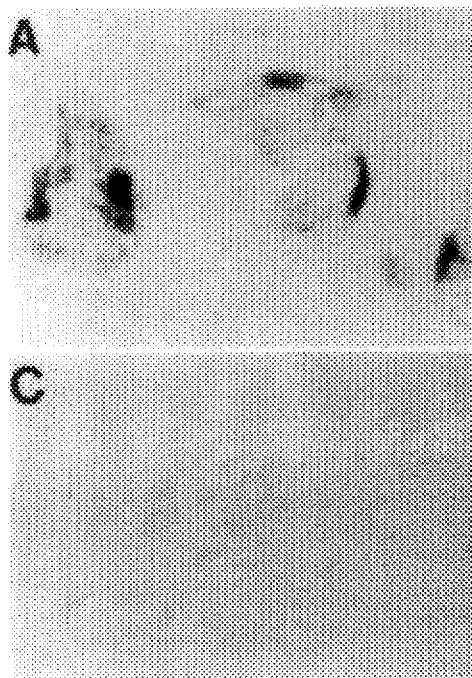
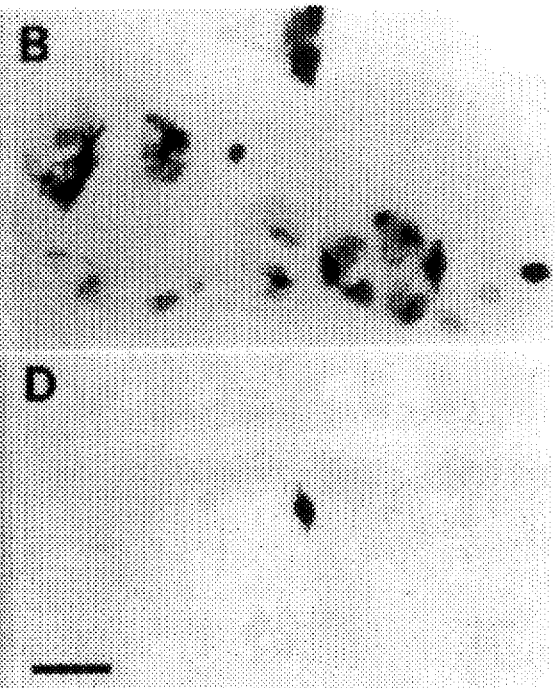
FIG. 6C
FIG. 6D
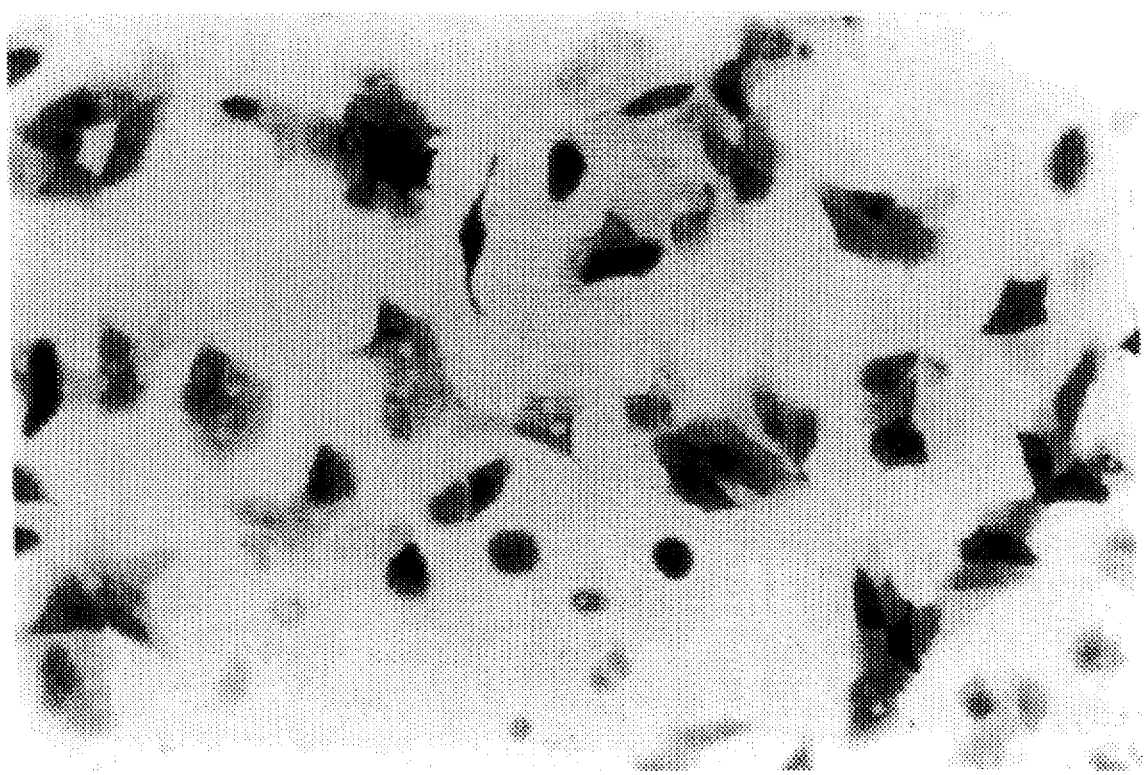
FIG. 7

NON-MAMMALIAN DNA VIRUS TO EXPRESS AN EXOGENOUS GENE IN A MAMMALIAN CELL

CROSS REFERENCE TO RELATED APPLICATION

This application is a continuation-in-part of U.S. patent application Ser. No. 08/311,157, filed Sep. 23, 1994.

BACKGROUND OF THE INVENTION

This invention relates to the use of a non-mammalian DNA virus to express an exogenous gene in a mammalian cell.

Current methods for expressing an exogenous gene in a mammalian cell include the use of mammalian viral vectors, such as those which are derived from retroviruses, adenoviruses, herpes viruses, vaccinia viruses, polio viruses, or adeno-associated viruses. Other methods of expressing an exogenous gene in a mammalian cell include direct injection of DNA, the use of ligand-DNA conjugates, the use of adenovirus-ligand-DNA conjugates, calcium phosphate precipitation, and methods which utilize a liposome- or polycation-DNA complex. In some cases, the liposome- or polycation-DNA complex is able to target the exogenous gene to a specific type of tissue, such as liver tissue. Some methods of targeting genes to liver cells utilize the asialoglycoprotein receptor (ASGP-R) which is present on the surface of hepatocytes (Spiess et al., 1990, Biochem. 29:10009–10018). The ASGP-R is a lectin which has affinity for the terminal galactose residues of glycoproteins. In these cases, the DNA complexes are endocytosed by the cell after they are bound to the ASGP-R on the cell surface.

The construction of viruses which are commonly used in gene expression (e.g., gene therapy) methods typically is based on the principle of removing unwanted functions from a virus that is known to infect, and replicate in, a mammalian cell. For example, the genes involved in viral replication and packaging often are removed to create a defective virus, and a therapeutic gene is then added. This principle has been used to create gene therapy vectors from many types of animal viruses such as retroviruses, adenoviruses, and herpes viruses. This method has also been applied to Sindbis virus, an RNA virus which normally infects mosquitoes but which can replicate in humans, causing a rash and an arthritis syndrome.

Non-mammalian viruses have been used to express exogenous genes in non-mammalian cells. For example, viruses of the family Baculoviridae (commonly referred to as baculoviruses) have been used to express exogenous genes in insect cells. One of the most studied baculoviruses is the *Autographa californica* multiple nuclear polyhedrosis virus (AcMNPV). Although some species of baculoviruses which infect crustacea have been described (Blissard, et al., 1990, Ann. Rev. Entomology 35:127), the normal host range of the baculovirus AcMNPV is limited to the order lepidoptera. Baculoviruses have been reported to enter mammalian cells, and baculoviral DNA has been detected in nuclear extracts of mammalian cells (Volkman and Goldsmith, 1983, Appl. and Environ. Microbiol. 45:1085–1093; Carbonell and Miller, 1987, Appl. and Environ. Microbiol. 53:1412–1417; Brusca et al., 1986, Intervirology 26:207–222; and Tjia et al., 1983, Virology 125:107–117). While one report of baculovirus-mediated gene expression in mammalian cells has appeared, the authors later attributed the apparent reporter gene activity to the reporter gene product being carried into the cell after a prolonged incubation of the cell with the virus (Carbonell et al., 1985, J. Virol. 56:153–160; and Carbonell and Miller, 1987, Appl. and Environ. Microbiol. 53:1412–1417). These authors reported that, when the exogenous gene gains access to the cell as part of the baculovirus genome, the exogenous gene is not expressed de novo. In addition to the Baculoviridae, other families of viruses naturally multiply only in invertebrates; some of these viruses are listed in Table 1.

Gene therapy methods are currently being investigated for their usefulness in treating a variety of disorders. Most gene therapy methods involve supplying an exogenous gene to overcome a deficiency in the expression of a gene in the patient. Other gene therapy methods are designed to counteract the effect a disease. Still other gene therapy methods involve supplying an antisense nucleic acid (e.g., RNA) to inhibit expression of a gene of the host cell (e.g., an oncogene) or expression of a gene from a pathogen (e.g., a virus).

Certain gene therapy methods are being examined for their ability to correct inborn errors of the urea cycle, for example (see, e.g., Wilson et al., 1992, J. Biol. Chem. 267: 11483–11489). The urea cycle is the predominant metabolic pathway by which nitrogen wastes are eliminated from the body. The steps of the urea cycle are primarily limited to the liver, with the first two steps occurring within hepatic mitochondria. In the first step, carbamoyl phosphate is synthesized in a reaction which is catalyzed by carbamoyl phosphate synthetase I (CPS-I). In the second step, citrulline in formed in a reaction catalyzed by ornithine transcarbamylase (OTC). Citrulline then is transported to the cytoplasm and condensed with aspartate into arginosuccinate by arginosuccinate synthetase (AS). In the next step, arginosuccinate lyase (ASL) cleaves arginosuccinate to produce arginine and fumarate. In the last step of the cycle, arginase converts arginine into ornithine and urea.

A deficiency in any of the five enzymes involved in the urea cycle has significant pathological effects, such as lethargy, poor feeding, mental retardation, coma, or death within the neonatal period (see, e.g., Emery et al., 1990, In: Principles and Practice of Medical Genetics, Churchill Livingstone, N.Y.). OTC deficiency usually manifests as a lethal hyperammonemic coma within the neonatal period. A deficiency in AS results in citrullinemia which is characterized by high levels of citrulline in the blood. The absence of ASL results in arginosuccinic aciduria (ASA), which results in a variety of conditions including severe neonatal hyperammonemia and mild mental retardation. An absence of arginase results in hyperarginemia which can manifest as progressive spasticity and mental retardation during early childhood. Other current used therapies for hepatic disorders include dietary restrictions; liver transplantation; and administration of arginine freebase, sodium benzoate, and/or sodium phenylacetate.

SUMMARY OF THE INVENTION

I have discovered that a non-mammalian DNA virus carrying an exogenous gene expression construct can be used to express the exogenous gene in a mammalian cell.

Accordingly, in one aspect, the invention features a method of expressing an exogenous gene in a mammalian cell(s), involving introducing into the cell a non-mammalian DNA virus (also referred to herein as a "virion") whose genome carries the exogenous gene, and allowing the cell to live under conditions such that the exogenous gene is expressed.

In a second aspect, the invention features a method of treating a gene deficiency disorder in a mammal (e.g., a human or a mouse), involving introducing into a cell a therapeutically effective amount of a non-mammalian DNA virus whose genome carries an exogenous gene, and allowing the cell to live under conditions such that the exogenous gene is expressed in the mammal.

The invention further features a method for treating hepatocellular carcinoma in a mammal, involving introducing into a cell (e.g., a hepatocyte) a non-mammalian DNA virus (e.g., a baculovirus) whose genome expresses a carcinoma-therapeutic gene (e.g., tumor necrosis factors, thymidine kinases, diphtheria toxin chimeras, and cytosine diaminases). Generally, either in vivo or in vitro methods may be used to introduce the virus into the cell. Preferably, the exogenous gene is operably linked to a promoter which is active in cells of the carcinoma, but not in other cells of the mammal. For example, the α-fetoprotein promoter is active in cells of hepatocellular carcinomas and in fetal tissue but it is otherwise not active in mature tissues. Accordingly, the use of such a promoter is preferred in this aspect of the invention.

In each aspect of the invention, the non-mammalian DNA virus, preferably, is an invertebrate virus. For example, the DNA viruses listed in Table 1 may be used in the invention. Preferably, the invertebrate DNA virus is a baculovirus, e.g., a nuclear polyhedrosis virus, such as an *Autographa californica* multiple nuclear polyhedrosis virus. If desired, the nuclear polyhedrosis virus may be engineered such that it lacks a functional polyhedron gene. Either or both the occluded form and budded form of virus (e.g., baculovirus) can be used.

TABLE 1

NON-MAMMALIAN DNA VIRUSES WHICH MAY BE USED IN THE INVENTION.[1]

I. FAMILY:

BACULOVIRUSES   BACULOVIRIDAE
SUBFAMILY:

OCCLUDED BACULOVIRUSES-   EUBACULOVIRINAE
VIRUSES
  Genus:

Nuclear polyhedrosis virus (NPV)
  Subgenus:

Multiple Nucleocapsid Viruses (MNPV)
    Preferred Species:

*Autographa californica* nuclear polyhedrosis virus (AcMNPV)
    Other Members:

*Choristoneura fumiferena* MNPV (CfMNPV)
    *Mamestra brassicae* MNPV (MbMNPV)
    *Orgyia pseudotsugata* MNPV (OpMNPV)
    and approximately 400–500 species isolated from seven insect orders and Crustacea.
  Subgenus:

Single Nucleocapsid Viruses (SNPV)
    Preferred Species

*Bombyx mori* S Nuclear Polyhedrosis Virus (BmSNPV)
    Other Members:

*Heliothis zea* SNPV (HzSnpv)
    *Trichoplusia ni* SNPV (TnSnpv)
    and similar viruses isolated from seven insect orders and Crustacea.

TABLE 1-continued

NON-MAMMALIAN DNA VIRUSES WHICH MAY BE USED IN THE INVENTION.[1]

Genus:

Granulosis virus (GV)
    Preferred Species:

*Plodia interpunctella* granulosis virus (PiGV)
    Other Members:

*Trichoplusia ni* granulosis virus (TnGV)
    *Pieris brassicae* granulosis virus (PbGV)
    *Artogeia rapae* granulosis virus (ArGV)
    *Cydia pomonella* granulosis virus (CpGV)
    and similar viruses from about 50 species in the Lepidoptera
SUBFAMILY:

NON-OCCLUDED BACULO-   NUDIBACULOVARINAE
VIRUSESVIRUSES
  Genus:

Non-occluded baculoviruses (NOB)
    Preferred Species:

*Heliothis zea* NOB (HzNOB)
    Other Members:

*Oryctes rhinoceros* virus
    Additional viruses have been observed in a fungus (*Strongwellsea magna*), a spider, the European crab (*Carcinus maenas*), and the blue crab (*Callinectes sapidus*).
II. FAMILY:

ICOSAHEDRAL CYTOPLASMIC   DEOXYTRIBOVIRUSES
                          IRIDOVIRIDAE
  Genus:

Small iridescent Iridovirus insect virus group
    Preferred Species:

Chilo iridescent virus
    Other Members:

| | |
    |---|---|
    | Insect iridescent virus 1 | Insect iridescent virus 2 |
    | Insect iridescent virus 6 | Insect iridescent virus 9 |
    | Insect iridescent virus 10 | Insect iridescent virus 16 |
    | Insect iridescent virus 17 | Insect iridescent virus 18 |
    | Insect iridescent virus 19 | Insect iridescent virus 20 |
    | Insect iridescent virus 21 | Insect iridescent virus 22 |
    | Insect iridescent virus 23 | Insect iridescent virus 24 |
    | Insect iridescent virus 25 | Insect iridescent virus 26 |
    | Insect iridescent virus 27 | Insect iridescent virus 28 |
    | Insect iridescent virus 29 | Insect iridescent virus 30 |
    | Insect iridescent virus 31 | Insect iridescent virus 32 |

Genus:

Large iridescent Chloroiridovirus insect virus group
    Preferred Species:

Moquito iridescent virus (iridescent virus - type 3, regular strain)
    Other Members:

| | |
    |---|---|
    | Insect iridescent virus 3 | Insect iridescent virus 4 |
    | Insect iridescent virus 5 | Insect iridescent virus 7 |
    | Insect iridescent virus 8 | Insect iridescent virus 11 |
    | Insect iridescent virus 12 | Insect iridescent virus 13 |
    | Insect iridescent virus 14 | Insect iridescent virus 15 |

Putative member:

*Chironomus plumosus* iridescent
  Genus:

Frog virus group   Ranavirus

TABLE 1-continued

NON-MAMMALIAN DNA VIRUSES WHICH MAY BE USED IN THE INVENTION.[1]

Preferred Species:

Frog virus 3 (FV3)
Other Members:

| | | | |
|---|---|---|---|
| Frog virus 1 | Frog virus 2 | Frog virus 5 | |
| Frog virus 6 | Frog virus 7 | Frog virus 8 | |
| Frog virus 9 | Frog virus 10 | Frog virus 11 | |
| Frog virus 12 | Frog virus 13 | Frog virus 14 | |
| Frog virus 15 | Frog virus 16 | Frog virus 17 | |
| Frog virus 18 | Frog virus 19 | Frog virus 20 | |
| Frog virus 21 | Frog virus 22 | Frog virus 23 | |
| Frog virus 24 | L2 | L4 | L5 |
| LT1 | LT 2 | LT 3 | LT 4 |
| T 21 | T 6 | T 7 | T 8 |
| T 9 | T 10 | T 11 | T 12 |
| T 13 | T 14 | T 15 | T 16 |
| T 17 | T 18 | T 19 | T 20 |

Tadpole edema virus from newts
Tadpole edema virus from *Rana catesbriana*
Tadpole edema virus from Xenopus Genus:

Lymphocystis disease virus group
Lymphocystisvirus
  Preferred Species:

Flounder isolate (LCDV-1)
Other Members:

Lymphocystis disease virus dab isolate (LCDV-2)
Putative member:

*Octopus vulgaris* disease virus

Genus

Goldfish virus group
  Preferred Species:

Goldfish virus 1 (GPV-1)
Other Member:

Goldfish virus 2 (GF-2)

III. FAMILY:

PARVOVIRIDAE
Genus

Insect parvovirus group Densovirus
  Preferred Species:

Galleria densovirus
Other Members:

Junonia Densovirus
Agraulis Densovirus
Bombyx Densovirus
Aedes Densovirus
Putative Members:

| | |
|---|---|
| Acheta Densovirus | Simulium Densovirus |
| Diatraea Densovirus | Euxoa Densovirus |
| Leucorrhinia Densovirus | Periplanata Densovirus |
| Pieris Densovirus | Sibine Densovirus |

PC 84 (parvo-like virus from the crab *Carcinus mediterraneus*)
Hepatopancreatic parvo-like virus of penaeid shrimp

IV. FAMILY:

| POXVIRUS GROUP | POXVIRIDAE |
|---|---|
| SUBFAMILY: | |
| POXVIRUSES OF VERTEBRATES | CHORDOPOXVIRINAE |

TABLE 1-continued

NON-MAMMALIAN DNA VIRUSES WHICH MAY BE USED IN THE INVENTION.[1]

Genus:

| | |
|---|---|
| *Molluscum contagiosum* subgroup | Molluscipoxvirus |

Preferred Species:

*Molluscum contagiosum* virus

SUBFAMILY:

| POXVIRUS OF INSECTS | ENTOMOPOXVIRINAE |
|---|---|

Putative Genus:

| Entomopoxvirus A | Poxvirus of Coleoptera |
|---|---|

Preferred Species:

Poxvirus of *Melolontha melolontha*
Other Members:

Coleoptera:

*Anomala cuprea*
*Aphodius tasmaniae*
*Demodema boranensis*
*Dermolepida albohirtum*
*Figulus sublaevis*
*Geotrupes sylvatious*

Putative Genus:

| Entomopoxvirus B | Poxvirus of Lepidoptera and Orthoptera |
|---|---|

Preferred Species:

Poxvirus of *Amsacta moorei* (Lepidoptera)
Other Members:

Lepidoptera:

*Acrobasis zelleri*
*Choristoneura biennis*
*Choristoneura conflicta*
*Choristoneura diversuma*
*Chorizagrotis auxiliaris*
*Operophtera brumata*

Orthoptera:

*Arphia conspersa*
*Locusta migratoria*
*Melanoplus sanguinipes*
*Oedaleus senugalensis*
*Schistocerca gregaria*

Putative Genus:

| Entomopoxvirus C | Poxvirus of Diptera |
|---|---|

Preferred Species:

Poxvirus of *Chironomus luridus* (Diptera)
Other Members:

Diptera:

*Aedes aegypti*
*Camptochironomus tentans*
*Chironomus attenuatus*
*Chironomus plumosus*
*Goeldichironomus holoprasimus*

Other members of family Poxviridae

Albatrosspox (Avipoxvirus)
Cotia
Embu
Marmosetpox
Marsupialpox (Australian 'quokkas')
Mule deer poxvirus (*Odocoileus hemionus*; Capripoxvirus)

TABLE 1-continued

NON-MAMMALIAN DNA VIRUSES WHICH MAY BE USED IN THE INVENTION.[1]

Volepox (*Microtus oeconomus*, *Microtus pennsylvanicus*)
Skunk poxvirus (*Mephitis mephitis*; Orthopoxvirus)

V. GROUP

CAULIFLOWR CAULIMOVIRUS MOSAIC VIRUS
Preferred Member:

Cauliflower mosaic virus (CaMV) (cabbage b, davis isolate)
Other Members:

| | |
|---|---|
| Blueberry red ringspot (327) | Carnation etched ring (182) |
| Dahlia mosaic (51) | Figwort mosaic |
| Horseradish latent | Mirabilis mosaic |
| Peanut chlorotic streak | Soybean chlorotic mottle (331) |
| Strawberry vein banding (219) | Thistle mottle |

Putative Members:

| | |
|---|---|
| Aquilegia necrotic mosaic | Cassava vein mosaic |
| Cestrum virus | Petunia vein clearing |
| Plantago virus 4 | Sonchus mottle |

VI. GROUP

GEMINIVIRUS
Subgroup I (i.e., Genus)

Maize streak virus
Preferred Member:

Maize streak virus (MSV) (133)
Other Members:

Chloris striate mosaic (221)
Digitaria streak
Miscanthus streak
Wheat dwarf
Putative Members:

Bajra streak
Bromus striate mosaic
Digitaria striate mosaic
Oat chlorotic strips
Paspalum striate mosaic Subgroup II (i.e., Genus):

Best curly top virus
Preferred Member:

Beet curly top virus (BCTV) (210)
Other Members:

Tomato pseudo-curly top virus
Bean summer death virus
Tobacco yellow dwarf virus
Tomato leafroll virus Subgroup III (i.e., Genus):

Bean golden mosaic virus
Preferred Member:

Bean golden mosaic virus (BGMV) (192)
Other Members:

| | |
|---|---|
| Abutilon mosaic virus | African cassava mosaic virus |
| Cotton leaf crumple virus | Euphorbia mosaic virus |
| Horsegram yellow mosaic virus | Indian cassava mosaic virus |
| Jatropha mosaic virus | Limabean golden mosaic virus |
| Malvaceous chlorosis virus | Melon leaf curl virus |
| Mungbean yellow mosaic virus | Potato yellow mosaic virus |
| Rhynochosia mosaic virus | Squash leaf curl virus |
| Tigre disease | Tobacco leaf curl virus |
| Tomato golden mosaic virus | Tomato leaf curl virus |
| Tomato yellow dwarf virus | Tomato yellow leaf curl virus |
| Tomato yellow mosaic virus | Watermelon curly mottle virus |
| Watermelon chlorotic stunt virus | |
| Honeysuckle yellow vein mosaic virus | |

Putative Members:

| | |
|---|---|
| Cotton leaf curl virus | Cowpes golden mosaic virus |
| Eggplant yellow mosaic virus | Eupatorium yellow vein virus |
| Lupin leaf curl virus | Soyabean crinkle leaf virus |
| Solanum apical leaf curl virus | Wissadula mosaic virus |

VII. FAMILY:
DsDNA ALGAL VIRUSES        PHYCODNAVIRIDAE
Genus:

dsDNA Phycovirus Phycodnavirus group
Preferred Species:

*Paramecium bursaria* chlorella virus - 1 (PBCV-1)
Viruses of:
*Paramecium bursaria* Chlorella NC64A viruses (NC64A viruses)
*Paramecium bursaria* Chlorella Pbi viruses (Pbi viruses)
*Hydra viridis* Chlorella viruses (HVCV)
Other Members:

Chlorella NC64A viruses (thirty-seven NC64A viruses, including PBCV-1)
Chlorella virus NE-8D (CV-NE8D; synonym NE-8D)

| | | |
|---|---|---|
| CV-NYb1 | CV-CA4B | CV-AL1A |
| CV-NY2C | CV-NC1D | CV-NC1C |
| CV-CA1A | CV-CA2A | CV-IL2A |
| CV-IL2B | CV-IL3A | CV-IL3D |
| CV-SC1A | CV-SC1B | CV-NC1A |
| CV-NE8A | CV-AL2C | CV-MA1E |
| CV-NY2F | CV-CA1D | CV-NC1B |
| CV-NYs1 | CV-IL5-2s1 | CV-AL2A |
| CV-MA1D | CV-NY2B | CV-CA4A |
| CV-NY2A | CV-XZ3A | CV-SH6A |
| CV-BJ2C | CV-XZ6E | CV-XZ4C |
| CV-XZ5C | CV-XZ4A | |

Chlorella Pbi viruses

| | | |
|---|---|---|
| CVA-1 | CVB-1 | CVG-1 |
| CVM-1 | CVR-1 | |

*Hydra viridis* Chlorella viruses

HVCV-1
HVCV-2
HVCV-3

VIII. FAMILY:

POLYDNAVIRUS GROUP        POLYDNAVIRIDAE
Genus:

Ichnovirus
Preferred Species

*Campoletis sonorensis* virus (CsV)

TABLE 1-continued

NON-MAMMALIAN DNA VIRUSES WHICH MAY BE USED IN THE INVENTION.[1]

Other Member:

Viruses of Glypta sp.
Genus:

Bracovirus
Preferred Species:

*Cotesia melanoscela* virus (CmV)

[1] These viruses are listed In: "Fifth Report of the International Committee on Taxonomy of Viruses" (ICTV) by Cornelia Buchen-Osmond, 1991, Research School of Biological Sciences, Canberra, Australia. Most viruses listed here are available from the American Type Culture Collection.

The genome of the non-mammalian DNA virus can be engineered to include one or more genetic elements, such as a promoter of a long-terminal repeat of a transposable element or a retrovirus (e.g., Rous Sarcoma Virus); an integrative terminal repeat of an adeno-associated virus; and/or a cell-immortalizing sequence, such as the EBNA-1 gene of Epstein Barr Virus (EBV). If desired, the genome of the non-mammalian DNA virus can include an origin of replication which functions in a mammalian cell (e.g., an EBV origin of replication or a mammalian origin of replication). The genome of the non-mammalian DNA virus used in the invention can include a polyadenylation signal and an RNA splicing signal positioned for proper processing of the product of the exogenous gene. In addition, the virus may be engineered to encode a signal sequence for proper targeting of the gene product.

Where cell-type specific expression of the exogenous gene is desired, the genome of the virus can include a cell-type-specific promoter, such as a liver cell-specific promoter. For example, the liver cell-specific promoter can include a promoter of a gene encoding albumin, α-1-antitrypsin, pyruvate kinase, phosphenol pyruvate carboxykinase, transferrin, transthyretin, α-fetoprotein, α-fibrinogen, or β-fibrinogen. Alternatively, a hepatitis B promoter may be used. If desired, a hepatitis B enhancer may be used in conjunction with a hepatitis B promoter. Preferably, an albumin promoter is used. An α-fetoprotein promoter is particularly useful for driving expression of an exogenous gene when the invention is used to express a gene for treating a hepatocellular carcinoma. Other preferred liver-specific promoters include promoters of the genes encoding the low density lipoprotein receptor, α2-macroglobulin, α1-antichymotrypsin, α2-HS glycoprotein, haptoglobin, ceruloplasmin, plasminogen, complement proteins (C1q, C1r, C2, C3, C4, C5, C6, C8, C9, complement Factor I and Factor H), C3 complement activator, β-lipoprotein, and α1-acid glycoprotein.

Essentially any mammalian cell can be used in the methods of the invention; preferably, the mammalian cell is a human cell. The cell may be a primary cell or it may be a cell of an established cell line. If desired, the virus may be introduced into a primary cell approximately 24 hours after plating of the primary cell to maximize the efficiency of infection. Preferably, the mammalian cell is a hepatocyte, such as a HepG2 cell or a primary hepatocyte; a cell of the kidney cell line 293; or a PC12 cell (e.g., a differentiated PC12 cell induced by nerve growth factor). Other preferred mammalian cells are those which have an asialoglycoprotein receptor. Additional preferred mammalian cells include NIH3T3 cells, HeLa cells, Cos7 cells, and $C_2C_{12}$ cells.

The virus can be introduced into the cell in vitro, or in vivo. Where the virus is introduced into a cell in vitro, the cell can subsequently be introduced into a mammal (e.g., into the portal vein or into the spleen), if desired. Accordingly, expression of the exogenous gene may be accomplished by allowing the cell to live or grow in vitro, in vivo, or in vitro and in vivo, sequentially. Similarly, where the invention is used to express an exogenous gene in more than one cell, a combination of in vitro and in vivo methods may be used to introduce the gene into more than one mammalian cell.

If desired, the virus may be introduced into the cell by administering the virus to a mammal which carries the cell. For example, the virus can be administered intravenously or intraperitoneally to such a mammal. If desired, a slow-release device, such as an implantable pump, may be used to facilitate delivery of the virus to a cell. Where the virus is administered to a mammal carrying the cell into which the virus will be introduced, the cell can be targeted by modulating the amount of the virus administered to the mammal and by controlling the method of delivery. For example, intravascular administration of the virus to the portal vein or to the hepatic artery may be used to facilitate targeting the virus to a liver cell. In another method, the virus may be administered to a cell or organ of a donor individual prior to transplantation of the cell or organ to a recipient.

Where the cell is allowed to live under in vitro conditions, conventional tissue culture conditions and methods may be used. In a preferred method, the cell is allowed to live on a substrate which contains collagen, such as Type I collagen or rat tail collagen, or a matrix containing laminin. Implantable versions of such substrates are also suitable for use in the invention (see, e.g., Hubbell et al., 1995, Bio/Technology 13:565–576 and Langer and Vacanti, 1993, Science 260: 920–925). As an alternative to, or in addition to, allowing the cell to live under in vitro conditions, the cell can be allowed to live under in vivo conditions (e.g., in a human).

A variety of exogenous genes may be used to encode gene products such as a proteins, antisense nucleic acids (e.g., RNAs), or catalytic RNAs. If desired, the gene product (e.g., protein or RNA) may be purified from the cell. Thus, the invention can be used in the manufacture of a wide variety of proteins that are useful in the fields of biology and medicine. The invention can also be used to treat a gene deficiency disorder, and particularly appropriate genes for expression include those genes which are expressed in normal cells of the type of cell to be infected, but expressed at a less than normal level in the particular cell to be infected. Particularly useful gene products include carbamoyl synthetase I, ornithine transcarbamylase; arginosuccinate synthetase, arginosuccinate lyase, and arginase. Other desirable gene products include fumarylacetoacetate hydrolase, phenylalanine hydroxylase, alpha-1 antitrypsin, glucose-6-phosphatase, low-density-lipoprotein receptor, and porphobilinogen deaminase, factor VIII, factor IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, pyruvate carboxylase, hepatic phosphorylase, phosphorylase kinase, glycine decarboxylase (also referred to as P-protein), H-protein, T-protein, Menkes disease protein, and the product of Wilson's disease gene PWD. Other examples of desirable genes for expression include those which encode tumor suppressors (e.g., p53), insulin, or CFTR (e.g., for treating cystic fibrosis). The therapeutic usefulness of the invention is not limited to correcting deficiencies in gene expression.

Where the invention is used to express an antisense RNA, the preferred antisense RNA is complementary to a nucleic acid (e.g., an mRNA) of a pathogen of the mammalian cell (e.g., a virus, a bacterium, or a fungus). For example, the invention can be used in a method of treating a hepatitis infection by expressing an antisense RNA which hybridizes to an mRNA of an essential hepatitis virus gene product (e.g., a polymerase mRNA). Other preferred antisense RNAs include those which are complementary to a naturally-occurring gene in the cell, but which genes are expressed at an undesirably high level. For example, an antisense RNA can be designed to inhibit expression of an oncogene in a mammalian cell. Similarly, the virus can be used to express a catalytic RNA (i.e., a ribozyme) which inhibits expression of a target gene in the cell by hydrolyzing an mRNA of the targeted gene product. Antisense RNAs and catalytic RNAs can be designed by employing conventional criteria.

By "non-mammalian" DNA virus is meant a virus which has a DNA genome (rather than RNA) and which is naturally incapable of replicating in a vertebrate, and specifically a mammalian, cell. Included are insect viruses (e.g., baculoviruses), avian viruses, plant viruses, and fungal viruses. Viruses which naturally replicate in prokaryotes are excluded. Examples of viruses that are useful in practicing the invention are listed in Table 1.

By "insect" DNA virus is meant a virus which has a DNA genome and which is naturally capable of replicating in an insect cell (e.g., Baculoviridae, Iridoviridae, Poxviridae, Polydnaviridae, Densoviridae, Caulimoviridae, and Phycodnaviridae).

By "positioned for expression" is meant that the DNA molecule which includes the exogenous gene is positioned adjacent to a DNA sequence which directs transcription and, if desired, translation of the DNA and RNA (i.e., facilitates the production of the exogenous gene product or an RNA molecule).

By "promoter" is meant minimal sequence sufficient to direct transcription. Also useful in the invention are those promoters which are sufficient to render promoter-dependent gene expression controllable for cell-type specificity, cell-stage specificity, or tissue-specificity (e.g., liver-specific promoters), and those promoters which are inducible by external signals or agents; such elements can be located in the 5' or 3' regions of the native gene.

By "operably linked" is meant that a gene and a regulatory sequence(s) (e.g., a promoter) are connected in such a way as to permit gene expression when the appropriate molecules (e.g., transcriptional activator proteins) are bound to the regulatory sequence(s).

By "exogenous" gene or promoter is meant any gene or promoter which is not normally part of the non-mammalian DNA virus (e.g., baculovirus) genome. Such genes include those genes which normally are present in the mammalian cell to be infected; also included are genes which are not normally present in the mammalian cell to be infected (e.g., related and unrelated genes of other cells or species).

By "cell immortalizing sequence" is meant a nucleic acid which when present in a cell is capable of transforming the cell for prolonged inhibition of senescence. Included are SV40 T-antigen, c-myc, telomerase, and E1A.

The invention is useful for expressing an exogenous gene(s) in a mammalian cell (e.g., a HepG2 cell). This method can be employed in the manufacture of proteins to be purified, such as proteins which are used pharmaceutically (e.g., insulin). The invention can also be used therapeutically. For example, the invention can be used to express in a patient a gene encoding a protein which corrects a deficiency in gene expression. In alternative methods of therapy, the invention can be used to express any protein, antisense RNA, or catalytic RNA in a cell.

The non-mammalian viral expression system of the invention offers several advantages. The invention allows for de novo expression of an exogenous gene; thus, detection of the exogenous protein (e.g., β-galactosidase) in an infected cell represents protein that was actually synthesized in the infected cell, as opposed to protein that is carried along with the virus aberrantly. The non-mammalian viruses used in the invention are not normally pathogenic to humans; thus, concerns about safe handling of these viruses are minimized. Similarly, because the majority of naturally-occurring viral promoters are not normally active in a mammalian cell, production of undesired viral proteins is inhibited. For example, PCR-based experiments indicate that some viral late genes are not expressed. Accordingly, in contrast to some mammalian virus-based gene therapy methods, the non-mammalian virus-based methods of the invention should not provoke a host immune response to the viral proteins. In addition, non-mammalian viruses can be propagated with cells grown in serum-free media, eliminating the risk of adventitious infectious agents present in the serum contaminating the virus preparation. In addition, the use of serum-free media eliminates a significant expense faced by users of mammalian viruses. Certain non-mammalian viruses, such as baculoviruses, can be grown to a high titer (i.e., $10^8$ pfu/ml). Generally, virus genomes are large (e.g., the baculovirus genome is 130 kbp); thus, viruses used in the invention can accept large exogenous DNA molecules. In certain embodiments, the invention employs a virus whose genome has been engineered to contain an exogenous origin of replication (e.g., the EBV oriP). The presence of such sequences on the virus genome allows episomal replication of the virus, increasing persistence in the cell. Where the invention is used in the manufacture of proteins to be purified from the cell, the invention offers the advantage that it employs a mammalian expression system. Accordingly, one can expect proper post-translational processing and modification (e.g., glycosylation) of the gene product.

Other features and advantages of the invention will be apparent from the following description of the preferred embodiments thereof, and from the claims.

DETAILED DESCRIPTION

The drawings will first be described. Drawing

Figures 4A, 4B:
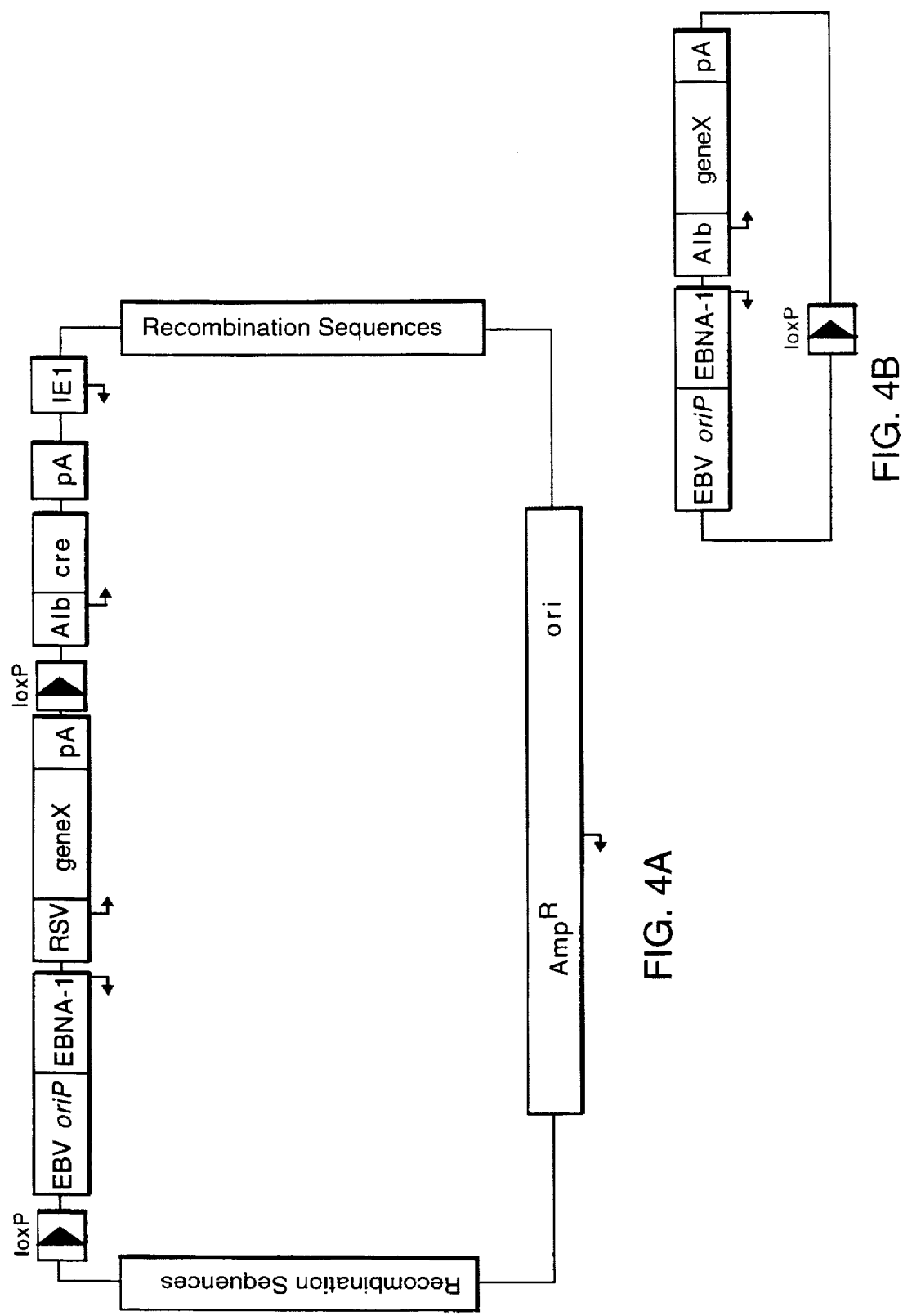

FIG. 4A is a schematic representation of a transfer plasmid which allows excision of a gene cassette. FIG. 4B is a schematic representation of the gene cassette excised by the transfer plasmid of FIG. 4A. Excision of the gene cassette is mediated by cre-lox recombination. This strategy allows persistence of an exogenous gene in the absence of viral sequences.

Figure 5:
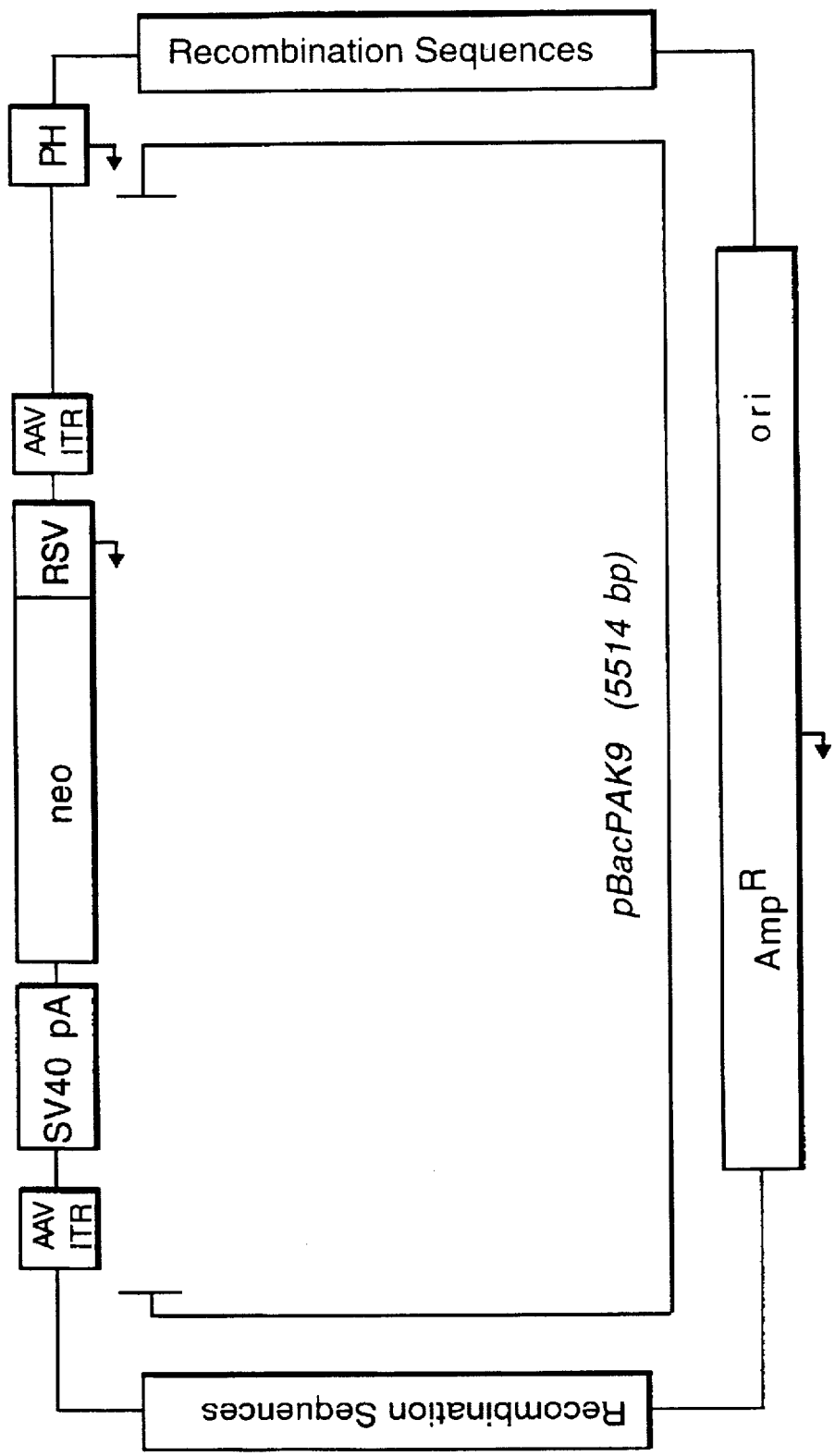

FIG. 5 is a schematic representation of the transfer plasmid, pBV-AVneo, a chimera of baculovirus and Adeno-associated virus sequences. This plasmid is capable of integrating into the genome of the infected cell.

FIG. 6A–6D is a photograph of cells which were stained with X-gal one day post-infection with an AcMNPV virus containing a RSV-lacZ cassette. Cells expressing the lacZ gene stain darkly with X-gal. FIG. 6A is a photograph of a typical field of HepG2 cells infected at a multiplicity of infection of 15. FIG. 6B is a photograph of a typical field of HepG2 cells infected at a multiplicity of infection of 125; over 25% of the cells were stained. FIG. 6C is a typical field of Sk-Hep-1 cells infected at a multiplicity of infection of 125, showing no positively-stained cells. FIG. 6D is a less typical field of Sk-Hep-1 cells infected at a multiplicity of infection of 125 showing a positively-stained cell. Bar=55 μm.

FIG. 7 is a photograph of cells obtained following baculovirus-mediated gene transfer into primary cultures of rat hepatocytes. Over 70% of the cells were stained blue.

Figure 8:
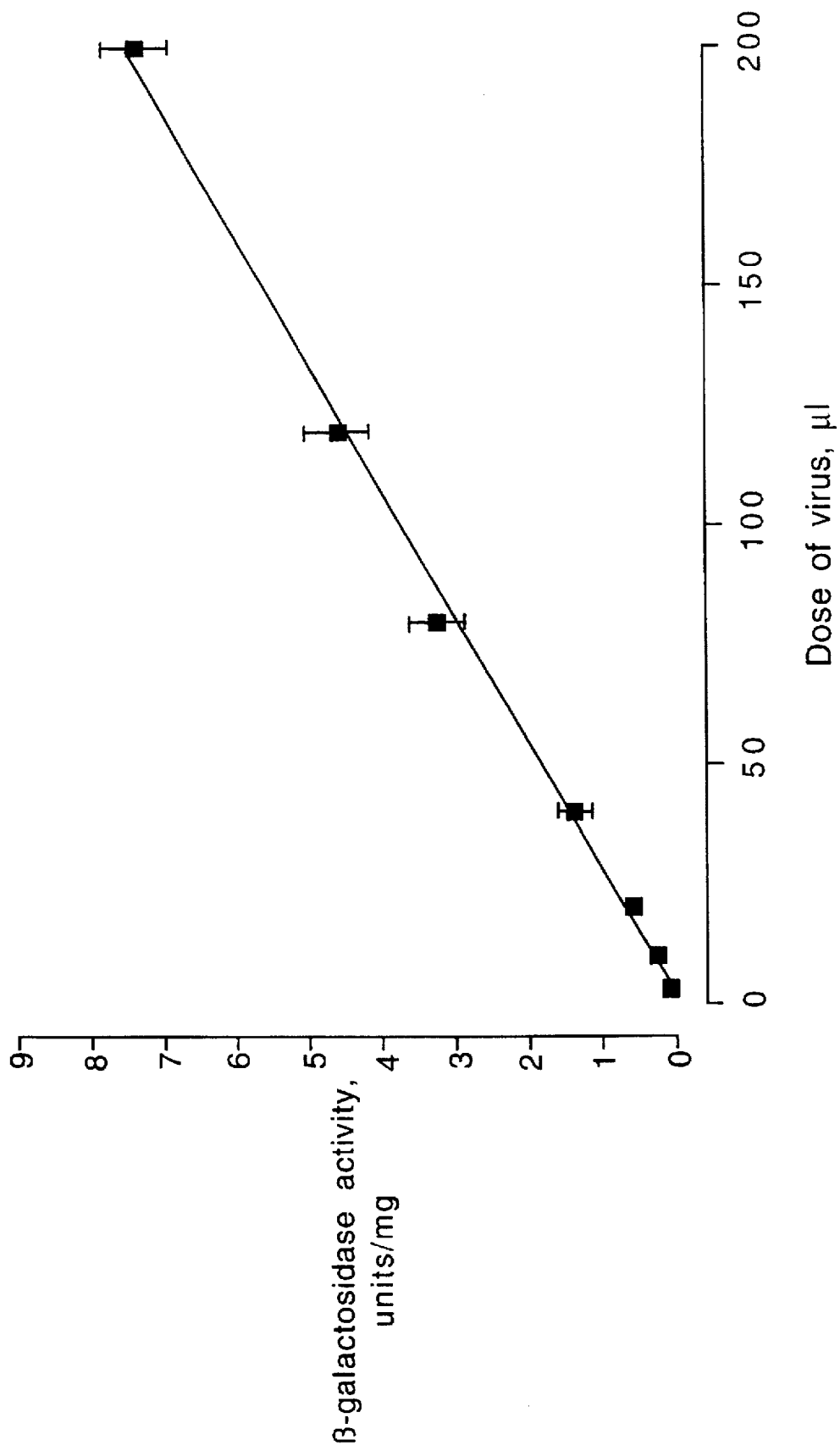

FIG. 8 is a graph displaying the dose-dependence of baculovirus-mediated gene transfer. Here, $10^6$ HepG2 cells were seeded into 60 mm petri dishes, and one day later the cells were exposed to the indicated dose of an AcMNPV virus containing a RSV-lacZ cassette (viral titer=$1.4 \times 10^9$ pfu/ml). One day post-infection the cells were harvested, and extracts were prepared and assayed for β-galactosidase enzyme activity. Extract activity is expressed in units of β-galactosidase activity as previously defined (Norton and Coffin, 1985, Mol. Cell. Biol. 5:281–290). Enzyme activity was normalized for the protein content of each extract. Each point is the average of three independent assays, with the error bars representing the standard deviation.

Figure 9:
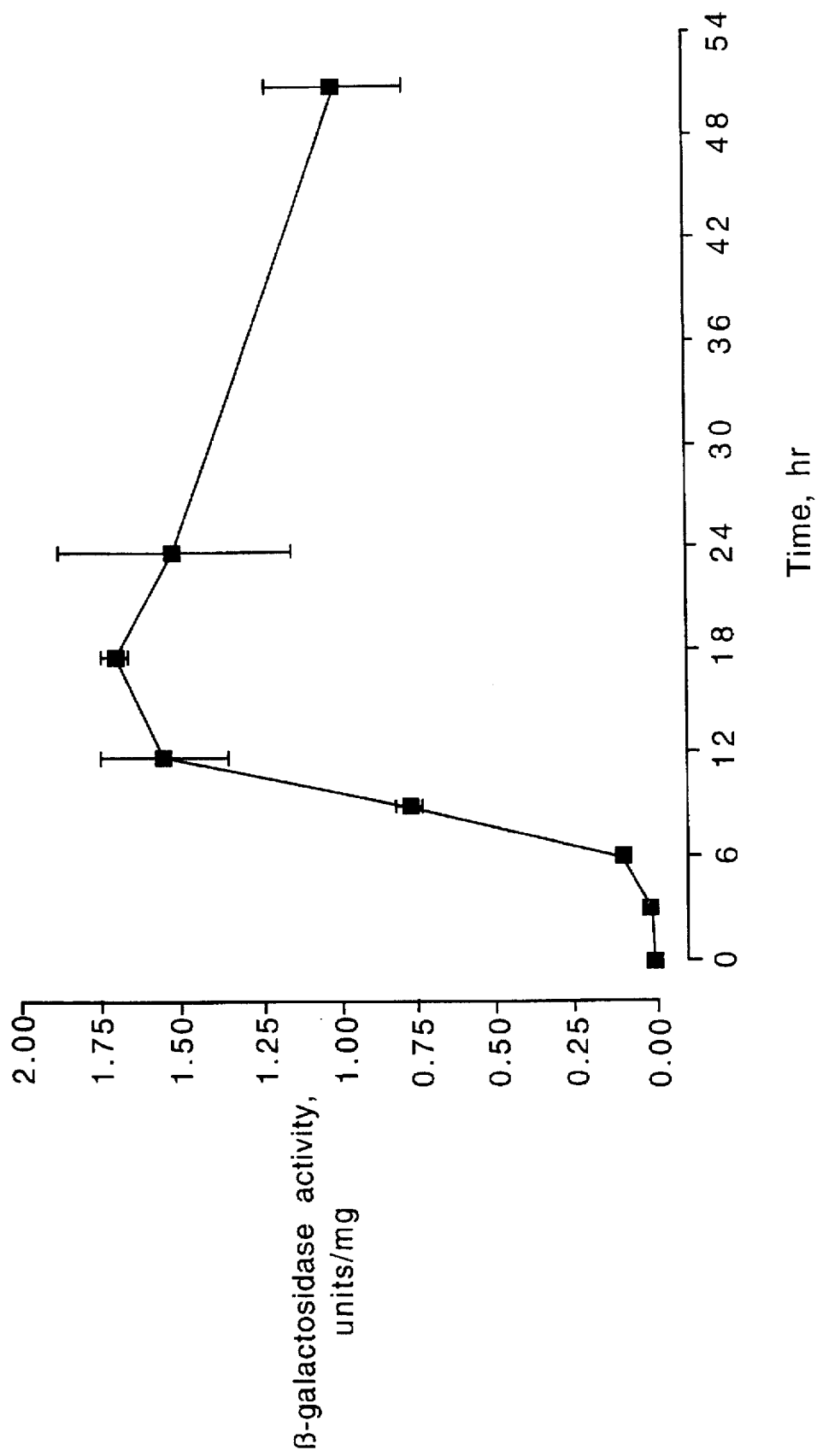

FIG. 9 is a graphic representation of results obtained in a time course of baculovirus-mediated expression. HepG2 cells were infected with AcMNPV virus containing a RSV-lacZ cassette (multiplicity of infection=15) at time zero. After one hour, the medium containing the virus was removed and replaced with fresh medium. Infected cells were harvested at the indicated time points and assayed for β-galactosidase activity as is described above. Each plotted point is expressed as the average of three independent assays, with the error bars representing the standard deviation. Expression from the virus peaked 12–24 hours post-infection and declined thereafter when normalized to total cellular protein.

I. GENETIC MANIPULATION OF VIRUSES

In contrast to conventional gene expression methods, the invention concerns modifying non-mammalian DNA viruses which do not naturally infect and replicate in mammalian cells. Thus, the invention is based on the addition of new properties to a non-mammalian DNA virus that allow it to deliver a gene to a mammalian cell, in contrast to conventional gene therapy vectors which are based on the principle of removing functions from the virus.

In the present method, the viral particle serves as a 'shell' for the delivery of DNA to the mammalian cell. The viral DNA is engineered to contain transcriptional control signals which are active in a mammalian cell to allow expression of the gene of interest. Conventional recombinant DNA techniques can be used for inserting such sequences. Because the non-mammalian DNA viruses used in the invention are not capable of replicating in mammalian cells, it is not necessary to delete essential viral functions to render them defective. Preferably, the genome of the virus used in the invention is normally transported to the nucleus in its natural host species because nuclear localization signals function similarly in invertebrate and in mammalian cells.

Preferably, the viral capsid or envelope contains a ligand which binds to mammalian cells to facilitate entry. Viruses propagated in invertebrate species (e.g., insects) do not normally terminate glycoproteins with sialic acid, and thus the viral ligand is often an asialoglycoprotein which binds to mammalian lectins (e.g., the hepatic asialoglycoprotein receptor), facilitating entry into mammalian cells. Alternatively, the viral particle may be modified by standard procedures (e.g., pseudotyping with VSV-G coat protein) to allow binding and entry into the mammalian cell. For example, the non-mammalian virus can contain a virion protein (e.g., the glycoprotein gp64 of AcMNPV) which facilitates fusion of the viral coat with the membrane of a mammalian cell, thus allowing entry of the viral particle into the cytosol.

In addition, it is preferred that the virus naturally replicate in a eukaryotic species. Examples of viruses which can be engineered to express exogenous gene in the invention are listed in Table 1.

Established methods for manipulating recombinant viruses may be incorporated into these new methods for expressing an exogenous gene in a mammalian cell. For example, viral genes can be deleted from the virus and supplied in trans via packaging lines. Deletion of such genes may be desired in order to (1) suppress expression of viral gene products which may provoke an immune response, (2) provide additional space in the viral vector, or (3) provide additional levels of safety in maintaining the virus in a cell.

Because most promoters of non-mammalian viruses are not active in mammalian cells, the exogenous gene should be operably linked to a promoter which is capable of directing gene expression in a mammalian cell. Examples of suitable promoters include the RSV LTR, the SV40 early promoter, the CMV IE promoter, the adenovirus major late promoter, and the Hepatitis B promoter. In addition, promoters which are cell-type-specific, stage-specific, or tissue-specific can be used. For example, several liver-specific promoters, such as the albumin promoter/enhancer, have been described (see, e.g., Shen et al., 1989, DNA 8:101–108; Tan et al., 1991, Der. Biol. 146:24–37; McGrane et al., 1992, TIBS 17:40–44; Jones et al., J. Biol. Chem. 265:14684–14690; and Shimada et al., 1991, FEBS Letters 279:198–200). Where the invention is used to treat a hepatocellular carcinoma, an α-fetoprotein promoter is particularly useful. This promoter is normally active only in fetal tissue; however, it is also active in liver tumor cells (Huber et al., 1991, Proc. Natl. Acad. Sci. 88:8039–8043). Accordingly, an α-fetoprotein promoter can be used to target expression of a liver-cancer therapeutic to liver tumor cells.

If desired, the virus genome can be engineered to carry an origin of replication in order to facilitate persistence of the exogenous gene in the mammalian cell. Origins of replication derived from mammalian cells have been identified (Burhans et al., 1994, Science 263:639–640). Other origins of replication, such as the Epstein-Barr Virus oriP, can also facilitate maintenance of expression in the presence of appropriate trans-acting factors, such as EBNA-1. If desired, the virus genome can be engineered to express more than one exogenous gene (e.g., the virus can be engineered to express OTC and AS).

Descriptions of several viruses which can be used in the invention now follow. These examples are provided for illustrative purposes, and are not meant to limit the scope of invention.

Figure 1:
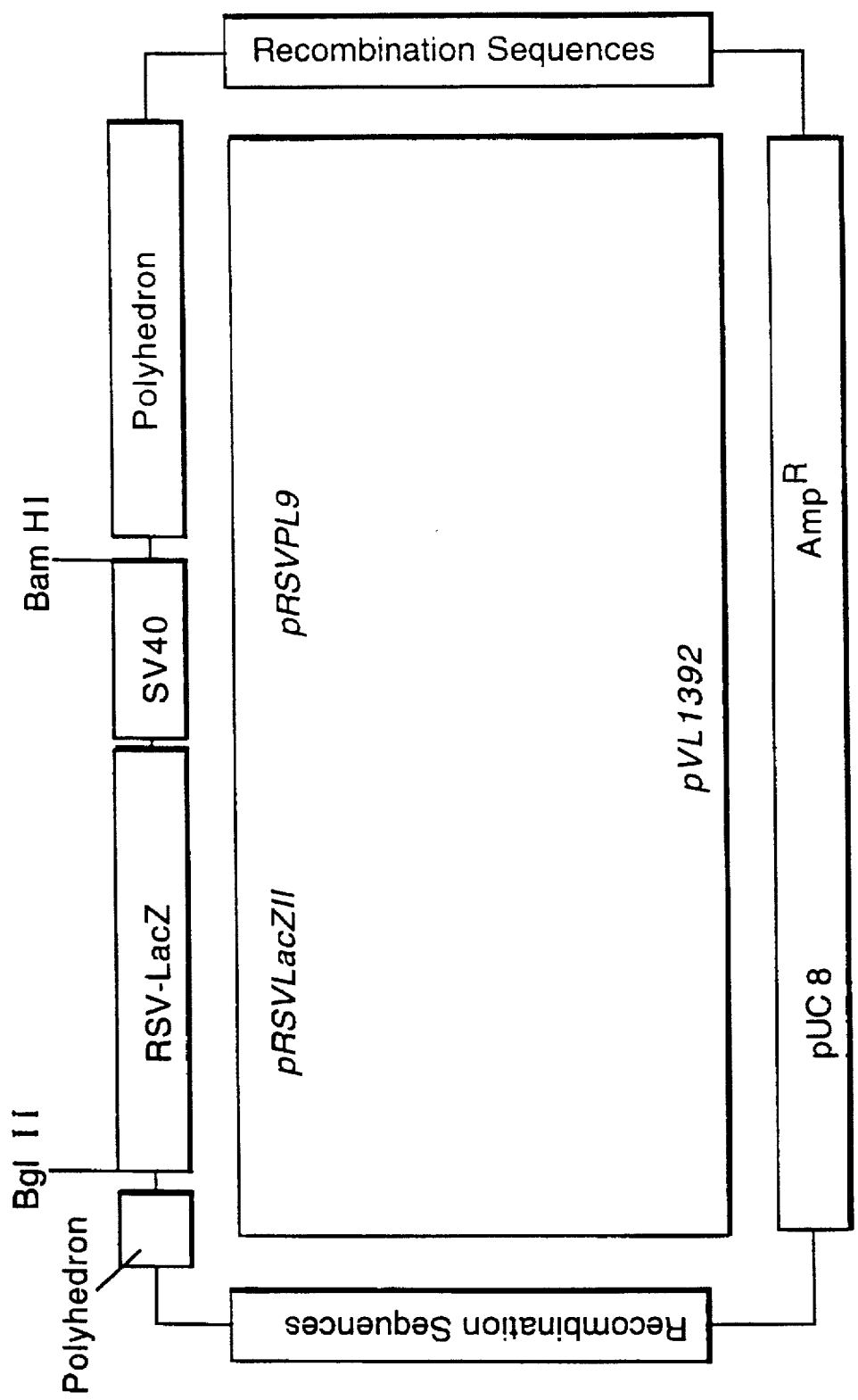
FIG. 1 is a schematic representation of the AcMNPV RSV-lacZ transfer plasmid Z4.

Construction of the Z4 Transfer Plasmid: Genetic manipulation of a baculovirus for use in the invention can be accomplished with commonly-known recombination techniques originally developed for expressing proteins in baculovirus (see, e.g., O'Reilly et al., 1992, In: Baculovirus expression vectors, W. H. Freeman, New York). In this example, an AcMNPV was constructed by interrupting the polyhedron gene of the virus with a cassette which directs expression of a reporter gene. The reporter gene cassette included DNA sequences corresponding to the Rous Sarcoma Virus (RSV) promoter operably linked to the *E. coli* lacZ gene (FIG. 1). The reporter gene cassette also included sequences encoding Simian Virus 40 (SV40) RNA splicing and polyadenylation signals.

The RSV-lacZ AcMNPV transfer plasmid used in several examples set forth below is named Z4 and was constructed as follows. An 847 bp fragment of pRSVPL9 including the SV40 RNA splicing signal and polyadenylation signal was excised using BglII and BamHI. Plasmid pRSVPL9 was derived from pRSVglobin (Gorman et al., Science 221:551–553) by digesting pRSVglobin with BglII, adding a HindIII linker, and then cleaving the DNA with HindIII. A double-stranded polylinker made by hybridization of the oligonucleotides 5'AGCTGTCGACTCGAGGTACCA-GATCTCTAGA3' (SEQ ID NO: 1) and 5'AGCTTCTA-GAGATCTGGTACCTCGAGTCGAC3' (SEQ ID NO: 2) was ligated to the 4240 bp fragment having the RSV promoter and SV40 splicing and polyadenylation signals. The resulting plasmid has the polylinker in place of the globin sequences. The SV40 sequence of pRSVPL9 was cloned into the BamHI site of pVL1392 (Invitrogen and Pharmingen) using standard techniques. The resulting intermediate plasmid was named pVL/SV40. An RSV-lacZ cassette was excised from pRSVlacZII (Lin et al., 1991, Biotechniques 11:344–348, and 350–351) with BglII and SpeI and inserted into the BglII and XbaI sites of pVL/SV40.

The AcMNPV RSV-lacZ virus, termed Z4, was prepared by homologous recombination of the Z4 transfer plasmid with linearized AcMNPV DNA. The AcMNPV virus used to prepare this DNA was AcV-EPA (Hartig et al., 1992, J. Virol. Methods 38:61–70).

Figure 2:
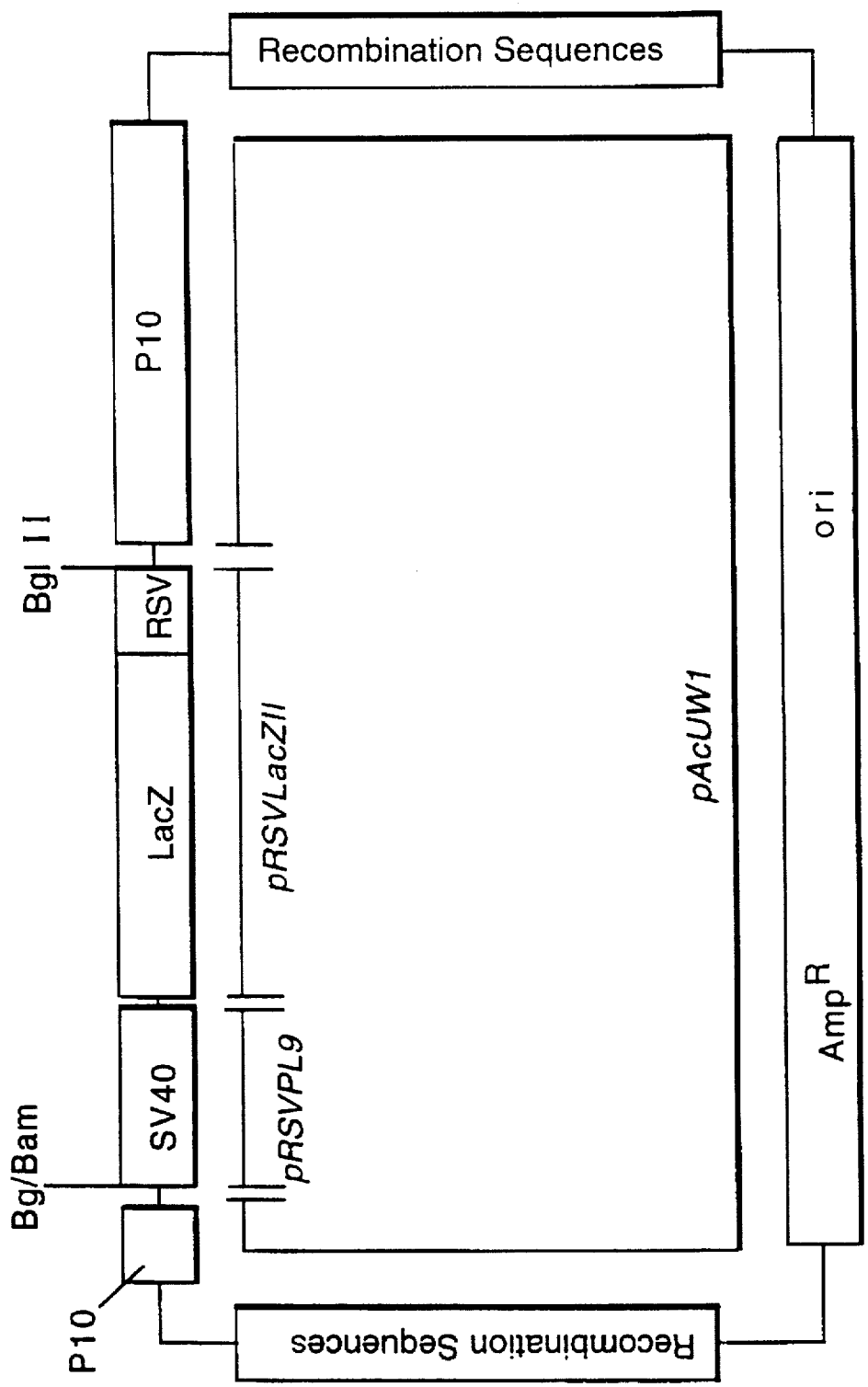
FIG. 2 is a schematic representation of the occluded AcMNPV RSV-lacZ transfer plasmid Z5.

Construction of the Z5 Transfer Plasmid: Certain non-mammalian viruses (e.g., baculoviruses) may be occluded in a protein inclusion body, or they may exist in a plasma membrane budded form. Where an occluded virus is used in the invention, the virus may first be liberated from the protein inclusion body, if desired. Conventional methods employing alkali may be used to release the virus (O'Reilly et al., 1992, In: Baculovirus expression vectors, W. H. Freeman, New York). An occluded, alkali-liberated baculovirus may be taken up by a cell more readily than is the non-occluded budded virus (Volkman and Goldsmith, 1983, Appl. and Environ. Microbiol. 45:1085–1093). To construct the Z5 transfer plasmid (FIG. 2), for using an occluded virus in the invention, the RSV-lacZ cassette was excised from the Z4 transfer plasmid using BglII and BamHI and then inserted into the BglII site of pAcUW1 (Weyer et al., 1990, J. Gen. Virol. 71:1525–1534).

Figure 3:
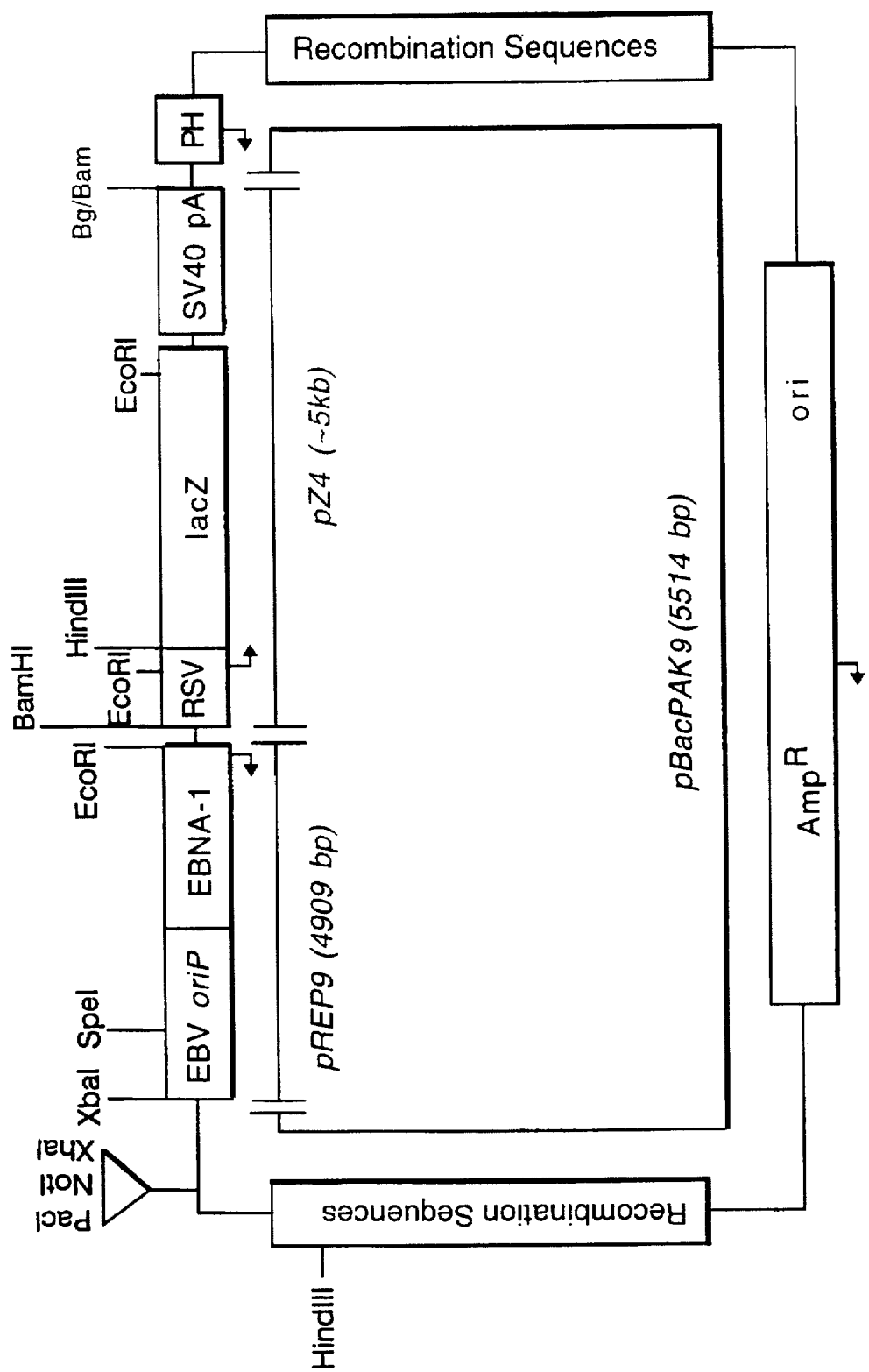
FIG. 3 is a schematic representation of the episomal transfer plasmid Z-EBV#1, a chimera of baculovirus and Epstein Barr Virus sequences. A virus produced with this transfer plasmid is capable of replicating in a cell.

Construction of the Z-EBV#1 Transfer Plasmid: The non-mammalian DNA viruses used in the invention may be engineered to permit episomal replication of the virus in the mammalian cell. Such a virus would persist longer, thereby optimizing methods for long-term expression of an exogenous gene in a cell. An example of such a replicating virus is Z-EBV#1 (FIG. 3), which was constructed as follows. The EBV oriP and EBNA-1 region was excised from pREP9 (Invitrogen) using EcoRI and XbaI and then inserted into the baculoviral transfer plasmid pBacPAK9 (Clontech) at its EcoRI and XbaI sites, yielding pEBVBP9. The RSV-lacZ cassette was then excised from transfer plasmid Z4 with BglII and BamHI and then inserted into the BamHI site of pEBVBP9 to yield the plasmid pZ-EBV#1.

Construction of Z4loxP: The Z4loxP viral genome is a substrate for recombination with bacteriophage P1 cre recombinase. This virus can be used to insert gene cassettes bearing a loxP site into the virus using standard procedures (Patel et al., 1992, Nucl. Acids Res. 20:97–104). A variation of this insertion system may be engineered so that the viral sequences are excised from the remaining gene expression sequences. For example, an auto-excising transfer plasmid may be constructed (FIG. 4) to express an exogenous gene in a mammalian cell. This plasmid contains loxP sequences which facilitate excision of the baculoviral sequences. The Z4loxP transfer plasmid was constructed by inserting a synthetic loxP site into the Z4 transfer plasmid. Two loxP oligonucleotides were synthesized and annealed to each other. The oligonucleotides were: 5'GATCTGAC-C T A A T A A C T T C G T A T A G C A T A C A T-TATACGAAGTTATATTAAGG3' (SEQ ID NO: 3) and 5'GATCCCTTAATATAACTTCGTATAATGT ATGC-TATACGAAGTTATTAGGTCA3' (SEQ ID NO: 4). The oligonucleotides were annealed by heating them to 80° C. in the presence of 0.25M NaCl and then allowing the mixture to cool slowly to room temperature before use in the ligation reactions. The annealed oligonucleotides were then ligated to the Z4 transfer plasmid which had been digested with BglII. The ligations and analysis of the resulting clones were performed with standard cloning techniques. Recombinant Z4loxP baculovirus was then generated with conventional methods for recombination into linear baculoviral DNA.

Construction of pBV-AVneo, an AAV Chimera Transfer Plasmid: A baculovirus genome which is capable of integrating into a chromosome of the host cell may also be used in the invention. Such an integrated virus may persist in the cell longer than a non-integrated virus. Accordingly, methods of gene expression involving such viruses may obviate the need for repeated administration of the virus to the cell, thereby decreasing the likelihood of mounting an immune response to the virus. The transfer plasmid pBV-AVneo (FIG. 5) includes the integrative terminal repeats of an Adeno-associated virus (AAV). This transfer plasmid was constructed by excising the BglII-BamHI fragment from pFasV.neo and inserting the fragment into the BamHI site of pAVgal in place of the lacZ gene. Plasmid pAVgal was constructed by replacing the rev and cap coding sequences of AAV with a CMV promoter and a lacZ gene. The resulting intermediate fragment, termed pAV.neo, was digested with PvuI, and the large PvuI fragment then was inserted into the PacI site of pBacPAK9. If desired, a suitable promoter operably linked to an AAV rep gene may be inserted into this construct (e.g., between the AAV ITR and the polyhedron promoter) to facilitate excision and recombination into the genome. Examples of rep genes which may be inserted into this construct include rep40, rep52, rep68, and rep78.

Propagation of Viruses: Conventional methods can be used to propagate the viruses used in the invention (see, e.g., Burieson, et al., 1992, Virology: A Laboratory Manual, Academic Press, Inc., San Diego, Calif. and Mahy, ed., 1985, Virology: A Practical Approach, IRL Press, Oxford, UK). For example, for baculoviruses used in the experiments described below, the virus was plaque purified and amplified according to standard procedures (see, e.g., O'Reilly et al. infra and Summers and Smith, 1987, A manual of methods for baculovirus vectors and insect cell culture procedures, Texas Agricultural Experiment Station Bulletin No. 1555, College Station, Tex.). AcMNPV and Sf21 cells were propagated by spinner culture in Hinks TNM-FH media (JRH Biosciences) containing 10% fetal bovine serum (FBS) and 0.1% PLURONIC F-68™. Amplified virus can be concentrated by ultracentrifugation in an SW28 rotor (24,000 rpm, 75 minutes) with a 27% (w/v) sucrose cushion in 5 mM NaCl, 10 mM Tris pH 7.5, and 10 mM EDTA. The viral pellet is then resuspended in phosphate-buffered saline (PBS) and sterilized by passage through a 0.45 μm filter (Nalgene). If desired, the virus may be resuspended by sonication in a cup sonicator. AcMNPV was titered by plaque assay on Sf21 insect cells.

II. Expression of an Exogenous Gene in a Mammalian Cell

Nearly all mammalian cells are potential targets of non-mammalian viruses, and any cultured cell can rapidly be tested.

Growth of cells: Conventional tissue culture methods can be used to grow mammalian cells to be infected (Freshney, 1987, Culture of Animal Cells: A Manual of Basic Techniques, 2nd ed., Alan R. Liss, Inc. New York, N.Y.). In the following example, the ability of the Z4 baculovirus to infect a variety of cells was tested. Included were HepG2, Sk-Hep-1, NIH3T3, HeLa, CHO/dhfr−, 293, COS, Ramos, Jurkat, HL60, K-562, $C_2C_{12}$ myoblasts, $C_2C_{12}$ myotubes, and nerve growth factor-differentiated PC12 cells. These cells were grown as follows. HepG2 and Sk-Hep-1 cells were cultured in minimal essential medium as modified by Eagle (EMEM) containing 10% FBS. NIH3T3, HeLa, 293, and COS cells were cultured in DMEM containing 10% FBS. CHO/dhfr-cells were cultured in MEM alpha containing 10% FBS. Ramos, Jurkat, HL60, and K-562 cells were cultured in RPMI 1640 medium containing 10% FBS. HL60 cells were induced to differentiate by culture in the same medium containing 0.5% dimethyl sulfoxide and 1 μM retinoic acid (Sigma). $C_2C_{12}$ myoblasts were propagated in DMEM containing 20% FBS and differentiated to myotubes during culture in DMEM containing 10% horse serum. PC12 cells were propagated in DMEM containing 5% FBS and 10% horse serum, and were induced to differentiate during culture in DMEM containing 10% FBS, 5% horse serum, and 100 ng/ml nerve growth factor. Cells were seeded one day prior to infection with AcMNPV, and multiplicities of infection were calculated assuming a doubling in cell number during this time.

In vitro Infection of Cells: In vitro infection of mammalian cells with a virus may be accomplished by allowing the virus to adsorb onto the cells for 0.1 to 6 hours; preferably, adsorption proceeds for 1 to 2 hours. Generally, a multiplicity of infection of 0.1 to 1,000 is suitable; preferably, the moi is 100 to 500. For relatively refractory cells, a moi of 100 to 1,000 is preferable. Generally, a titer of 10 to 200 pfu/cell is desirable. For the viruses used in the invention, the titer may be determined with conventional methods which employ the non-mammalian cells which the virus naturally infects. If desired, the mammalian cell to be infected may be maintained on a matrix which contains collagen (e.g., rat tail Type I collagen). Based on cell counting after culture and infection of cells on collagen-coated plates and comparison with cells grown on a conventional EHS matrix, I have found that a collagen matrix increases the susceptibility of cells (e.g., liver cells) to infection by a non-mammalian virus by 10 to 100 fold, relative to a conventional EHS matrix. Commercially-available plates containing a collagen matrix are available (e.g., BIO-COAT™ plates, Collaborative Research), and rat tail collagen is also commercially available (Sigma Chemical and Collaborative Research).

In the in vitro assays described below, standard conditions for infection utilized $2 \times 10^6$ cells and RSV-lacZ AcMNPV at a moi of 15. Adherent cell lines were seeded one day prior to infection. Cells were exposed to virus in 2 ml of medium for 90 minutes, and then the virus-containing medium was removed and replaced with fresh medium. Mock-infected cells were treated with 2 ml medium lacking the viral inoculum.

Detection of infection and Gene Expression: Delivery of a virus to a cell and expression of the exogenous gene can be monitored using standard techniques. For example, delivery of a virus (e.g., AcMNPV) to a cell can be measured by detecting viral DNA or RNA (e.g., by Southern or Northern blotting, slot or dot blotting, or in situ hybridization, with or without amplification by PCR). Suitable probes which hybridize to nucleic acids of the virus, regulatory sequences (e.g., the promoter), or the exogenous gene can be conveniently prepared by one skilled in the art of molecular biology. Where the invention is used to express an exogenous gene in a cell in vivo, delivery of the virus to the cell can be detected by obtaining the cell in a biopsy. For example, where the invention is used to express a gene in a liver cell(s), a liver biopsy can be performed, and conventional methods can be used to detect the virus in a cell of the liver.

Expression of an exogenous gene in a cell of a mammal can also be followed by assaying a cell or fluid (e.g., serum) obtained from the mammal for RNA or protein corresponding to the gene. Detection techniques commonly used by molecular biologists (e.g., Northern or Western blotting, in situ hybridization, slot or dot blotting, PCR amplification, SDS-PAGE, immunostaining, RIA, and ELISA) can be used to measure gene expression. If desired, a reporter gene (e.g., lacZ) can be used to measure the ability of a particular baculovirus to target gene expression to certain tissues or cells. Examination of tissue can involve: (a) snap-freezing the tissue in isopentane chilled with liquid nitrogen; (b) mounting the tissue on cork using O.C.T. and freezing; (c) cutting the tissue on a cryostat into 10 μm sections; (d) drying the sections and treating them with paraformaldehyde; (e) staining the tissue with X-gal (0.5 mg/ml)/ferrocyanide (35 mM)/ferricyanide (35 mM) in PBS; and (f) analyzing the tissue by microscopy.

In the following example, I measured the ability of a baculovirus to infect fourteen different types of mammalian cells. In this example, the baculovirus was the Z4 virus, prepared by homologous recombination of the Z4 transfer plasmid with linearized AcMNPV DNA. The tested cells were HepG2, Sk-Hep-1, NIH3T3, HeLa, CHO/dhfr−, 293, COS, Ramos, Jurkat, HL60, K-562, $C_2C_{12}$ myoblasts, $C_2C_{12}$ myotubes, and nerve growth factor-differentiated PC12 cells, and these cells were grown and infected as is described above. $C_2C_{12}$ and PC12 cells may have increased in cell number during differentiation and therefore reflect a somewhat lower moi.

To measure expression of the reporter gene in the infected cells, colorimetric assays of β-galactosidase enzymatic activity were performed with standard methods (Norton et al., 1985, Molecular & Cellular Biology 5:281–290). Other conventional methods for measuring β-galactosidase activity could be used in lieu of the methods employed in this example. Cell extracts were prepared at one day post-infection. Cell monolayers were rinsed three times with PBS, scraped from the dish, and collected by low-speed centrifugation. The cell pellets were resuspended in 25 mM Tris pH 7.4/0.1 mM EDTA and then subjected to three cycles of freezing in liquid nitrogen and thawing in a 37° C. water bath. The extracts were then clarified by centrifugation at 14,000×g for 5 minutes. Standard conditions for assaying β-galactosidase activity utilized 0.1 ml of cell extract, 0.8 ml of PM-2 buffer, and 0.2 ml of o-nitrophenyl-α-D-galactopyranoside (4 mg/ml) in PM-2 buffer for 10 minutes at 37° C. (Norton et al., 1985, Mol. & Cell. Biol. 5:281–290). The reaction was stopped by the addition of 0.5 ml of 1M sodium carbonate. The amount of substrate hydrolyzed was detected spectrophotometrically at 420 nm, and β-galactosidase enzymatic activity was calculated with conventional methods (Norton et al., 1985, Mol. & Cell. Biol. 5:281–290). The assay was verified to be linear with respect to extract concentration and time. Extract protein concentrations were determined using the Coomassie Plus protein assay (Pierce) with bovine serum albumin as a standard, and the level of β-galactosidase activity was expressed as units of β-galactosidase activity per mg of protein. Other standard protein assays can be used, if desired.

For histochemical staining of β-galactosidase activity, cells were fixed in 2% (w/v) formaldehyde-0.2% (v/v) paraformaldehyde in PBS for 5 minutes. After several rinses with PBS, the cells were stained by the addition of 0.5 mg/ml of X-gal (BRL) in PBS for 2–4 hours at 37° C.

Of the 19 mammalian cell lines examined, three of the cell lines (HepG2, 293, and PC12) showed statistically significant ($P<0.05$, Student's t-test) higher β-galactosidase activity in extracts after exposure to the virus (Table 2). The human liver tumor line HepG2 exposed to the RSV-lacZ baculovirus expressed greater than 80-fold higher levels of β-galactosidase than mock-infected controls. The adenovirus-transformed human embryonal kidney cell line 293 expressed the lacZ reporter gene at a level of about four-fold over background. In addition, PC12 cells, which were differentiated to a neuronal-like phenotype with nerve growth factor, exhibited about two-fold higher β-galactosidase levels after infection with the RSV-lacZ baculovirus. This difference was statistically significant ($P=0.019$).

By histochemical staining, a more sensitive assay, β-galactosidase activity was detected in 14 of the 19 cell lines exposed to virus. Thus, certain of the cell lines which did not yield statistically significantly higher levels of β-galactosidase, as measured in extracts, were, in fact, able to express β-galactosidase at low, but reproducible, frequencies, as detected by the more sensitive X-gal staining procedure. This frequency could be increased by using higher multiplicities of infection such that cells which, at a low moi appear not to express the gene, stain blue at a higher moi. Examples of cell lines which could be transfected in this manner include SK-Hep-1, NIH3T3, HeLa, CHO/dhfr⁻, 293, Cos, and $C_2C_{12}$ cells. In addition, β-glaactosidase activity was detected in primary human muscle myoblasts which were exposed to virus. This finding indicates that baculovirus was able to mediate gene transfer both to primary cells and the corresponding established cell line ($C_2C_{12}$), indicating that expression of the exogenous gene in an established cell line has predictive value for the results obtained with primary cells. β-galactosidase activity was also detected in Hep3B cells treated with the virus; the level of expression in these cells was nearly equivalent to the level detected with HepG2 cells. In addition, β-galactosidase activity was found in FTO2B (rat hepatoma) cells and Hepa1-6 (human hepatoma) cells exposed to virus. β-galactosidase activity was also detected in NIH3T3 cells which were engineered to express the asialoglycoprotein receptor on the cell surface. These cells expressed approximately two times the level of β-galactosidase as did normal NIH3T3 cells. This observation suggests that an asiaoglycoprotein receptor may be used to increase susceptibility to viral-mediated gene transfer.

At the moi employed, the Ramos, Jurkat, HL60, and K-562 cell lines did not express statistically significant levels of β-galactosidase, as revealed by β-galactosidase enzyme assays after infection. Based on the results with other mammalian cell lines, it is expected that β-galactosidase activity would be detected in these apparently refractory cell lines when a higher dose (i.e., moi) of virus or longer adsorption time period is utilized.

Even when exposure of cells to the virus results in expression of the exogenous gene in a relatively low percentage of the cells (in vitro or in vivo), the invention can be used to identify or confirm the cell- or tissue-type specificity of the promoter which drives expression of the exogenous gene (e.g., a reporter gene such as a chloramphenicol acetyltransferase gene, an alkaline phosphatase gene, a luciferase gene, or a green fluorescent protein gene). Once identified, such a promoter may be employed in any of the conventional methods of gene expression. Similarly, only relatively low levels of expression are necessary for provoking an immune response (i.e., produce antibodies) in a mammal against the heterologous gene product. Thus, the gene expression method of the invention can be used in the preparation of antibodies against a preferred heterologous antigen by expressing the antigen in a cell of a mammal. Such antibodies may be used inter alia to purify the heterologous antigen. The gene expression method may also be used to elicit an immunoprotective response in a mammal (i.e., be used as a vaccine) against a heterologous antigen. In addition, the invention can be used to make a permanent cell line from a cell in which the virus mediated expression of a cell-immortalizing sequence (e.g., SV40 T antigen).

TABLE 2

BACULOVIRUS-MEDIATED EXPRESSION OF AN RSV-LACZ REPORTER GENE IN MAMMALIAN CELL LINES.

| | β-galactosidase activity (units/mg) Mean ± SD | |
|---|---|---|
| Cell Line | Mock Infected | RSV-lacZ Virus |
| HepG2 | 0.030 ± 0.004 | 2.628 ± 0.729 |
| Sk-Hep-1 | 0.019 ± 0.003 | 0.019 ± 0.004 |
| NIH3T3 | 0.026 ± 0.003 | 0.023 ± 0.005 |
| HeLa | 0.034 ± 0.009 | 0.036 ± 0.005 |
| CHO/dhfr- | 0.020 ± 0.002 | 0.026 ± 0.005 |
| 293 | 0.092 ± 0.014 | 0.384 ± 0.024 |
| COS | 0.029 ± 0.002 | 0.032 ± 0.007 |
| Ramos | 0.008 ± 0.002 | 0.011 ± 0.004 |
| Jurkat | 0.012 ± 0.004 | 0.007 ± 0.001 |
| HL60 | 0.042 ± 0.039 | 0.014 ± 0.015 |
| K-562 | 0.018 ± 0.006 | 0.017 ± 0.002 |
| $C_2C_{12}$ myoblast | 0.015 ± 0.001 | 0.014 ± 0.003 |
| $C_2C_{12}$ myotube | 0.049 ± 0.011 | 0.042 ± 0.004 |
| PC12 (+NGF) | 0.019 ± 0.005 | 0.033 ± 0.004 |

Histochemical staining using X-gal provided a highly sensitive method for detecting β-galactosidase expression in cells exposed to the modified AcMNPV. When HepG2 cells were exposed to the modified AcMNPV at a moi of 15, about 5–10% of the cells stained with X-gal (FIG. 6A). At a multiplicity of infection (moi) of 125, about 25–50% of the cells were stained (FIG. 6B). No adverse effects of exposure to the virus, such as nuclear swelling, were observed. These data demonstrate that the modified AcMNPV is highly effective at gene transfer into HepG2 cells when a sufficient dose of virus is used. When the Sk-Hep-1 line was exposed to virus at a moi of 15, no stained cells were observed (data not shown). While the majority of Sk-Hep-1 cells which were exposed to virus at a moi of 125, did not stain blue (FIG. 6C), a few cells were found that stained darkly after treatment with this higher doses of virus (FIG. 6D). These data indicate that cells which appear to be refractory to the virus at a relatively low moi can, in fact, be infected, and express the exogenous gene, at a higher moi. Stained cells were not found in mock-infected cultures (data not shown). The frequency of stained cells in the Sk-Hep-1 cell line was estimated to be 2,000–4,000 fold less than in HepG2 cells after exposure to equivalent doses of the modified virus, as determined by cell counting. Thus, the cell type-specificity demonstrated by the modified AcMNPV is relative rather than absolute. These data also indicate that, where a mixture of cells is contacted with the virus (in vitro or in vivo), the dosage of the virus can be adjusted to target the virus to the cells which are infected at a lower moi.

Expression of an Exogenous Gene in Primary Cultures of Rat Hepatocytes: A non-mammalian DNA virus can also be used to express an exogenous gene at high levels in primary cultures of rat hepatocytes. In this experiment, freshly prepared rat hepatocytes were plated onto dishes coated with rat tail collagen as previously described (Rana et al., 1994, Mol. Cell. Biol. 14:5858–5869). After 24 hours, the cells were fed with fresh medium containing RSV-lacZ baculovirus at a multiplicity of infection of approximately 430. After an additional 24 hours, the cells were fixed and stained with X-gal. Over 70% of the cells were stained blue, indicating that they have taken up and expressed the RSV-lacZ cassette (FIG. 7). The frequency of expression obtained in this example is higher than the frequency reported with conventional viral vectors used in gene therapy (e.g., retroviral and Herpes Simplex Virus vectors). Mock-infected cultures did not contain any positively-stained cells (data not shown). Other preferred exogenous genes can be used in lieu of the lacZ gene. In addition, other primary cells can readily be plated and incubated with a non-mammalian cell in lieu of the primary rat hepatocytes.

Dose-response of Baculovirus-mediated Gene Transfer: The histochemical data presented above indicate that increasing amounts of β-galactosidase are produced after exposure of mammalian cells to increasing amounts of virus. To quantitate the dose-dependence of baculovirus-mediated gene expression, HepG2 cells were exposed to increasing doses of virus and assayed for β-galactosidase enzyme activity. The amount of enzyme produced was linearly related to the inoculum of virus used over a wide range of doses (FIG. 8). This suggests that entry of each virus particle occurs independently of entry of other virus particles. The maximum dose of virus used in this assay was limited by the titer and volume of the viral stock, and no plateau in the amount of expression was observed using higher doses of virus. Accordingly, these data indicate that, in practicing the invention, one can modulate the level expression (i.e., the percent of cells in which the exogenous gene is expressed) by adjusting the dosage of virus used.

Time course of baculovirus-mediated gene transfer: HepG2 cells were exposed to the RSV-lacZ virus for 1 hour, after which the cells were harvested at various times and quantitatively assayed for β-galactosidase activity. As is shown in FIG. 9, β-galactosidase activity was detected as early as 6 hours after exposure to the virus, and expression peaked 12–24 hours post-infection. As is expected for an episomal DNA molecule, expression from the RSV-lacZ cassette gradually subsided at later time (FIG. 9 and data not shown). LacZ expression remained detectable by X-gal staining at 12 days post-transfection in fewer than 1 in 1,000 cells (data not shown). This expression of LacZ was not the result of viral spread, because culture supernatants taken from HepG2 cells 10 days post-infection had titers of 10 pfu/ml as determined by plaque assay on Sf21 cells. These data suggest that, where the invention is used in the manufacture of proteins which are purified from HepG2 cells, it may be desirable to isolate the protein from the cell at a time not sooner than 6 hours after infection of the cell. Depending on the half-life of the protein, it may be desirable to isolate the protein shortly after the peak in protein expression (i.e., after approximately 24 hours post-infection for HepG2 cells). The optimal time period for maximizing isolating the manufactured protein can readily be determined for each protein, virus, and cell.

Expression occurs de novo in mammalian cells: To confirm that the detected reporter gene activity in the mammalian cells was not simply the result of β-galactosidase being physically associated with AcMNPV virions as they enter the mammalian cell, several experiments were performed which demonstrate that the observed expression of the lacZ reporter gene was the result of de novo synthesis of β-galactosidase. First, the RSV-lacZ virus inoculum was assayed for β-galactosidase activity, and the level of β-galactosidase activity was found to be less than 10% of that expressed after infection of HepG2 cells. Second, HepG2 cells were infected with the RSV-lacZ virus and then cultured in the presence of the protein synthesis inhibitor cycloheximide. Inclusion of cycloheximide after infection inhibited the accumulation of β-galactosidase enzyme activity by more than 90% (Table 3). Third, HepG2 cells were infected at an equivalent moi with BacPAK6 (Clontech), a baculovirus in which the lacZ gene was under control of the viral polyhedron promoter rather than the RSV promoter (Table 3). The latter virus expresses extremely high levels of β-galactosidase activity in insect cells where the promoter is active (data not shown). In mammalian cells, the viral polyhedron promoter is inactive, and the virus containing this promoter failed to provide any enzyme activity in mammalian cells (Table 3). In contrast to prior studies of baculovirus interactions with mammalian cells, these data demonstrate that de novo synthesis of lacZ occurs after baculovirus-mediated gene transfer into a mammalian cell.

TABLE 3

BACULOVIRUS-MEDIATED GENE TRANSFER OCCURS DE NOVO.

| Virus | Drug During Infection | Drug Post Infection | β-galactosidase (% of RSV-lacZ, mean ± SD) |
|---|---|---|---|
| RSV-lacZ | none | none | 100 ± 5.8 |
| none | none | none | 3.2 ± 0.4 |
| RSV-lacZ | none | cycloheximide | 10.3 ± 1.0 |
| BacPAK6 | none | none | 2.8 ± 0.4 |
| RSV-lacZ | chloroquine | chloroquine | 2.9 ± 0.1 |
| RSV-lacZ | none | chloroquine | 25.1 ± 6.2 |

Baculovirus-mediated gene transfer is inhibited by lysomotropic agents: To gain insight into the mechanism by which baculoviruses express an exogenous gene in a mammalian cell, the susceptibility of gene expression to a lysomotropic agent was examined. Like other enveloped viruses, the budded form of AcMNPV normally enters cells via endocytosis, followed by low pH-triggered fusion of the viral envelope with the endosomal membrane, thus allowing escape into the cytoplasm (Blissard et al., 1993, J. Virol. 66:6829–6835; Blissard et al., 1990, Ann. Rev. of Entomol. 35:127–155). To determine whether endosome acidification was necessary for baculovirus-mediated gene transfer into mammalian cells, HepG2 cells were infected with RSV-lacZ AcMNPV in the presence of chloroquine, a lysomotropic agent. HepG2 cells were exposed to AcMNPV virus in media containing or lacking inhibitor for 90 minutes, then the virus-containing media were removed and replaced with fresh media containing or lacking inhibitors as listed.

One day post-infection, the cells were harvested and extracts were assayed for β-galactosidase activity and protein content. Each value in the table represents the average of three independent assays, with the amount of β-galactosidase produced by the RSV-lacZ AcMNPV virus in the absence of inhibitors assigned a value of 100%. β-galactosidase activity was normalized for protein content of each extract. When 25 μM chloroquine was continuously present during and after exposure of HepG2 cells to the virus, de novo expression of β-galactosidase was completely prevented (Table 3). This suggests that baculovirus-mediated gene transfer is dependent upon endosomal acidification. When chloroquine was added to the cells at 90 minutes after exposure to the virus, only partial inhibition of β-galactosidase expression was observed. Apparently, a portion (≈22%) of the viral particles were able to proceed through the endosomal pathway during the 90 minutes of exposure to the virus.

Baculovirus is Not Affected by Guinea Pig Complement: The ability of certain retroviruses to infect mammalian cells is inhibited by complement, which lyses the membrane of the virion (see, e.g., Rother et al., 1995, Human Gene Therapy 6:429–435). Accordingly, for intravascular administration of a virus to a mammal, it is preferred that the virus not be affected by complement. To determine whether components of guinea pig complement could inhibit the ability the Z4 virus to infect cells, 20 μl of the Z4 virus was diluted in 2 ml of restored guinea pig complement (BRL) or, as a control, 2 ml of the restoring solution (6% sodium acetate, 2% boric acid, and 0.25% sodium azide; BRL) in the absence of complement. The mixture then was incubated at 37° C. for 10 minutes then serially diluted (two 100-fold dilutions) in serum-free TNM-FH insect media. A 100 μl aliquot of each viral stock was then used to infect a monolayer of Sf9 insect cells, and the monolayer was overlayed with media containing 1.5% low melting point agarose, according to conventional baculovirus titering methods. After 7 days, the viral plaques were visualized by staining with MTT (see, e.g., Shanafelt, 1991, BioTechniques 11:330). The plate of cells which contained the virus that was exposed to complement was estimated to contain 430 plaques, representing a viral titer of $4.3 \times 10^9$ pfu/ml. The control plate had approximately 260 plaques, representing a viral titer of $2.6 \times 10^9$ pfu/ml. These results indicate that no significant diminution of viral titer was found in the samples exposed to complement, suggesting that intravascular administration of the virus will be an effective means for delivering the virus in vivo.

Analysis of RNA Expression From Viral Promoters in HepG2 Cells: One advantage of using a non-mammalian virus to express an exogenous gene in a mammalian cell is that, due to a lack of appropriate host cell factors, the non-mammalian viral promoters may not be active in the mammalian cell. To determine whether AcMNPV viral gene are expressed in HepG2 cells, the viral RNA was analyzed. In these experiments, HepG2 cells were infected with the Z4 virus at a moi of approximately 30. At 18 hours post-infection, the cells were harvested, and total cellular RNA was extracted from the cells. The total cellular RNA was analyzed by Northern blotting for expression of viral genes. The probe included a 1.7 kbp PacI-SalI fragment from pAcUW1 (Pharmingen) which contains the viral late gene, p74, as well as the very late (hyperexpressed) gene, p10. Total cellular RNA from Z4-infected Sf9 insect cells was employed as a positive control. While extremely strong signals were detected for p10 and p74 for the control insect cells, no signal was observed for Z4-infected HepG2 cells or uninfected control cells.

Additional experiments which used reverse transcriptase-PCR (RT-PCR), a highly sensitive method, provided further evidence that the majority of viral genes are not transcribed in the mammalian HepG2 cells. RT-PCR analysis was preformed with RNA prepared from Z4-infected HepG2, uninfected HepG2, or infected Sf9 cells at 6 or 24 hours post-infection. HepG2 cells were infected at a moi of 10 or 100. At 6 hours post-infection, no RT-PCR product was observed from the viral p39, ETL, LEF1, IE1, or IE-N genes at either dose of virus in Z4-infected HepG2 cells. In contrast, RT-PCR products were readily detected in Z4-infected Sf9 cells. At 24 hours post-infection, no expression of these gene was detected in HepG2 cells infected at a moi of 10. At 24 hours post-infection, no expression of the viral p39, ETL, or LEF1 genes was observed in HepG2 cells infected at an moi of 100. However, at this high does of virus, low levels of expression from the viral IE1 and IE-N genes was observed. The low level of expression detected at an moi of 100 was nonetheless significantly lower than the level of expression in insect cells. Expression of these genes may result from recognition of the viral TATA box by mammalian transcription factors (i.e., transcription of the immediate early genes by RNA polymerase II (see, e.g., Hoopes and Rorhman, 1991, Proc. Natl. Acad. Sci. 88:4513–4517). In contrast to the immediate early genes, the late viral genes are transcribed by a virally-encoded RNA polymerase which, instead of requiring a TATA box, initiates transcription at a TAAG motif (O'Reilly et al., supra). Accordingly, expression of the viral late genes is naturally blocked in mammalian cells. If desired, expression of the immediate early genes can be blocked by deleting those genes, using conventional methods.

The data set forth above suggest that a receptor(s) on the surface of the infected mammalian cell may mediate, though not necessarily be required for, infection of the mammalian cell. Candidate cell lines of particular interest include those which express a cell-surface asialoglycoprotein receptor (ASGP-R). HepG2 cells differ from Sk-Hep-1 human hepatocytes and NIH3T3 mouse fibroblast cells by the presence of ASGP-R on the cell surface. In these studies, β-galactosidase was expressed in fewer Sk-Hep-1 cells (FIG. 6B) or NIH3T3 cells than HepG2 cells. The lacZ gene was expressed in HepG2 cells at a frequency estimated as greater than 1,000 fold more than that in Sk-Hep-1 cells, based on quantitative counts of X-gal stained cells. Normal hepatocytes have 100,000 to 500,000 ASGP-R, with each receptor internalizing up to 200 ligands per day. The ASGP-R may facilitate entry of the virus into the cell by providing a cell-surface receptor for glycoproteins on the virion. The glycosylation patterns of insect and mammalian cells differ, with the carbohydrate moieties on the surface of the virion produced in insect cells lacking terminal sialic acid. Those carbohydrate moieties may mediate internalization and trafficking of the virion. In addition to the ASGP-R, other galactose-binding lectins exist in mammals (see, e.g., Jung et al., 1994, J. Biochem. (Tokyo) 116:547–553) may mediate uptake of the virus.

If desired, the ASGP-R can be expressed on the surface of a cell to be infected by the virus (e.g., baculovirus). The genes encoding the ASGP-R have been cloned (Spiess et al., 1985, J. Biol. Chem. 260:1979 and Spiess et al., 1985, PNAS 82:6465), and standard retroviral, adeno-associated virus, or adenoviral vectors or chemical methods can be used for expression of the ASGP-R in the cell to be infected by a virus. Other receptors for ligands on the virion, such as receptors for insect carbohydrates can also be expressed on the surface of the mammalian cell to be infected to facilitate infection (see, e.g., Monsigny et al., 1979, Biol. Cellulaire 33:289–300). Alternatively, the virion can be modified through chemical means (see, e.g., Neda, et al., 1991, J. Biol. Chem. 266:14143–14146) or other methods, such as pseudotyping (see, e.g., Burns et al., 1993, PNAS 90:8033–8037), to enable the virion to bind to other receptors on the mammalian cell. For example, viral coat proteins such as the *Vesicular stomatitis* virus G glycoprotein (VSV-G), or the influenza virus hemagglutinin protein can be used for pseudotyping. Alternatively, fusions between the viral coat proteins (e.g., gp64) and a targeting molecule (e.g., VSV-G or VCAM) can be expressed on the virion. Overexpression of a membrane protein, such as a cell adhesion molecule (e.g., VCAM), in insect packaging cells also can facilitates targeting of the virus to a mammalian cell. In addition, non-receptor-mediated events can mediate uptake of the virus by the cell, leading to expression of an exogenous gene in the mammalian cell.

III. Therapeutic Use of a Non-mammalian Virus Expressing an Exogenous Gene

The discovery that a non-mammalian DNA virus efficiently expressed a lacZ reporter gene in several mammalian cells indicates that a non-mammalian DNA virus can be used therapeutically to express an exogenous gene in a cell of a mammal. For example, the method of the invention can facilitate expression of an exogenous gene in a cell of a patient for treatment of a disorder that is caused by a deficiency in gene expression. Numerous disorders are known to be caused by single gene defects (see Table 4), and many of the genes involved in gene deficiency disorders have been identified and cloned. Using standard cloning techniques (see, e.g., Ausubel et al., *Current Protocols in Molecular Biology*, John Wiley & Sons, (1989)), a non-mammalian virus can be engineered to express a desired exogenous gene in a mammalian cell (e.g., a human cell).

TABLE 4

EXAMPLES OF DISORDERS WHICH CAN BE TREATED WITH THE INVENTION AND GENE PRODUCTS WHICH CAN BE MANUFACTURED WITH THE INVENTION

| Gene Product | Disorder |
| --- | --- |
| fumarylacetoacetate hydrolase | hereditary tyrosinemia |
| phenylalanine hydroxylase | phenylketonuria |
| LDL receptor | familial hypercholesterolemia |
| alpha-1 antitrypsin | alpha-1 antitrypsin deficiency |
| glucose-6-phosphatase | glycogen storage diseases |
| porphobilinogen deaminase | diseases caused by errors in porphyrin metabolism, e.g., acute intermittent porphyria |
| CPS-I, OTC, AS, ASL, or arginase | disorders of the urea cycle |
| factors VIII & IX | hemophilia |
| cystathione β-synthase | homocystinuria |
| branched chain ketoacid decarboxylase | maple syrup urine disease |
| albumin | hypoalbuminemia |
| isovaleryl-CoA dehydrogenase | isovaleric acidemia |
| propionyl CoA carboxylase | propionic acidemia |
| methyl malonyl CoA mutase | methylmalonyl acidemia |
| glutaryl CoA dehydrogenase | glutaric acidemia |
| insulin | insulin-dependent diabetes |
| β-glucosidase | Gaucher's disease |
| pyruvate carboxylase | pyruvate carboxylase deficiency |
| hepatic phosphorylase or phosphorylase kinase | glycogen storage diseases |
| glycine decarboxylase, H-protein, or T-protein | non-ketotic hyperglycinemias |
| product of Wilson's disease gene pWD | Wilson's disease |
| Menkes disease protein | Menkes disease |

TABLE 4-continued

EXAMPLES OF DISORDERS WHICH CAN BE TREATED WITH THE INVENTION AND GENE PRODUCTS WHICH CAN BE MANUFACTURED WITH THE INVENTION

| Gene Product | Disorder |
| --- | --- |
| cystic fibrosis transmembrane conductance regulator | cystic fibrosis |

The invention can also be used to facilitate the expression of a desired gene in a cell having no obvious deficiency. For example, the invention can be used to express insulin in a hepatocyte of a patient in order to supply the patient with insulin in the body. Other examples of proteins which can be expressed in a mammalian cell (e.g., a liver cell) for delivery into the system circulation of the mammal include hormones, growth factors, and interferons. The invention can also be used to express a regulatory gene or a gene encoding a transcription factor (e.g., a VP16-tet repressor gene fusion) in a cell to control the expression of another gene (e.g., genes which are operably-linked to a tet operator sequence; see, e.g., Gossen et al., 1992, PNAS 89:5547–5551). If desired, a tumor suppressor gene, such as the gene encoding p53, can be expressed in a cell in a method of treating cancer. In addition, the invention can be used to treat a hepatocellular carcinoma by expressing in a cell a hepatocellular carcinoma-therapeutic gene. For example, genes such as those encoding tumor necrosis factors, thymidine kinases, diphtheria toxin chimeras, and cytosine diaminases can be expressed in a method of treating a hepatocellular carcinoma (see, e.g., Vile and Russell, 1994, Gene Therapy 1:88–98). In treating a hepatocellular carcinoma, it is particularly desirable to operably link the exogenous gene to an α-fetoprotein promoter because this promoter is active in cells of hepatocellular carcinomas, but not in normal mature cells.

Other useful gene products include RNA molecules for use in RNA decoy, antisense, or ribozyme-based methods of inhibiting gene expression (see, e.g., Yu et al., 1994, Gene Therapy 1: 13–26). If desired, the invention can be used to express a gene, such as cytosine deaminase, whose product will alter the activity of a drug or prodrug, such as 5-fluorocytosine, in a cell (see, e.g., Harris et al., 1994, Gene Therapy 1: 170–175). Methods such as the use of ribozymes, antisense RNAs, transdominant repressors, polymerase mutants, or core or surface antigen mutants can be used to suppress hepatitis viruses (e.g., hepatitis virus A, B, C, or D) in a cell. Other disorders such as familial hemachromatosis can also be treated with the invention by treatment with the normal version of the affected gene.

Preferred genes for expression include those genes which encode proteins that are expressed in normal mammalian cells (e.g., hepatocytes or lung cells). For example, genes encoding enzymes involved in the urea cycle, such as the genes encoding carbamoyl phosphate synthetase (CPS-I), ornithine transcarbamylase (OTC), arginosuccinate synthetase (AS), arginosuccinate lyase (ASL), and arginase are useful in this method. All of these genes have been cloned (for OTC, see Horwich et al., 1984, Science 224:1068–1074 and Hata et al., 1988, J. Biochem (Tokyo) 103:302–308; for AS, see Bock et al., 1983, Nucl. Acids Res. 11:6505; Surh et al., 1988, Nucl. Acids Res. 16:9252; and Dennis et al., 1989, PNAS 86:7947; for ASL, see O'Brien et al., 1986, PNAS 83:7211; for CPS-I, see Adcock et al., 1984, (Abstract) Fed. Proc. 43:1726; for arginase, see Haraguchi et al., PNAS 84:412). Subcloning these genes into a baculovirus can be readily accomplished with common techniques.

The therapeutic effectiveness of expressing an exogenous gene in a cell can be assessed by monitoring the patient for known signs or symptoms of a disorder. For example, amelioration of OTC deficiency and CPS deficiency can be detected by monitoring plasma levels of ammonium or orotic acid. Similarly, plasma citrulline levels provide an indication of AS deficiency, and ASL deficiency can be followed by monitoring plasma levels of arginosuccinate. Parameters for assessing treatment methods are known to those skilled in the art of medicine (see, e.g., Maestri et al., 1991, J. Pediatrics, 119:923–928).

The non-mammalian virus (e.g., baculovirus) can be formulated into a pharmaceutical composition by admixture with a pharmaceutically acceptable non-toxic excipient or carriers (e.g., saline) for administration to a mammal. In practicing the invention, the virus can be prepared for use in parenteral administration (e.g., for intravenous injection (e.g., into the portal vein)), intra-arterial injection (e.g., into the femoral artery or hepatic artery), intraperitoneal injection, intrathecal injection, or direct injection into an area (e.g., intramuscular injection). In particular, the non-mammalian virus can be prepared in the form of liquid solutions or suspensions. The virus can also be prepared for intranasal or intrabronchial administration, particularly in the form of nasal drops or aerosols.

In practicing the invention, the virus may be used to infect a cell outside of the mammal to be treated (e.g., a cell in a donor mammal or a cell in vitro), and the infected cell then is administered to the mammal to be treated. In this method, the cell can be autologous or heterologous to the mammal to be treated. For example, an autologous hepatocyte obtained in a liver biopsy can be used (see, e.g., Grossman et al., 1994, Nature Genetics 6:335). The cell can then be administered to the patient by injection (e.g., into the portal vein). In such a method, a volume of hepatocytes totaling about 1%–10% of the volume of the entire liver is preferred. Where the invention is used to express an exogenous gene in a liver cell, the liver cell can be delivered to the spleen, and the cell can subsequently migrate to the liver in vivo (see, e.g., Lu et al., 1995, Hepatology 21:7752–759). If desired, the virus may be delivered to a cell by employing conventional techniques for perfusing fluids into organs, cells, or tissues (including the use of infusion pumps and syringes). For perfusion, the virus is generally administered at a titer of $1 \times 10^6$ to $1 \times 10^{10}$ pfu/ml (preferably $1 \times 10^9$ to $1 \times 10^{10}$ pfu/ml) in a volume of 1 to 500 ml, over a time period of 1 minute to 6 hours.

The optimal amount of virus or number of infected cells to be administered to a mammal and the frequency of administration are dependent upon factors such as the sensitivity of methods for detecting expression of the exogenous gene, the strength of the promoter used, the severity of the disorder to be treated, and the target cell(s) of the virus. Generally, the virus is administered at a multiplicity of infection of about 0.1 to 1,000; preferably, the multiplicity of infection is about 5 to 100; more preferably, the multiplicity of infection is about 10 to 50.

Use of a Non-mammalian Virus to Express an Exogenous Gene In Vivo: In two experiments, I have detected lacZ expression in vivo following administration of a non-mammalian virus to two distinct animal models. In the first experiment, 0.5 ml of Z4 virus ($\approx 1.4 \times 10^9$ pfu/ml) was injected (at a rate of $\approx 1$ ml/min) into the portal vein of a single rat. At approximately 72 hours after infection, lacZ expression was detectable in at least one liver cell of the cryosections that were examined by conventional histochemical methods. The efficiency of expression may be increased by any one, or a combination of, the following procedures: (1) pre-treating the animal with growth factors; (2) partial hepatectomy, (3) administration of immunosuppressants to suppress any immune response to the virus; (4) use of a higher titer or dose of the virus; (5) infusion of the virus by surgical perfusion to the liver (e.g., in order to limit possible non-specific binding of the virus to red blood cells); and/or (6) sonication of the virus to minimize clumping of the virus.

In the second experiment, the Z4 virus was injected into via the tail vein of 3 eight week-old female BALB/c mice. In this case, the mice received either (i) $6 \times 10^7$ pfu virus in 0.15 ml phosphate buffered saline (PBS), (ii) $6 \times 10^8$ pfu virus in 0.15 ml PBS, or (iii) $2 \times 10^8$ pfu virus in 0.05 ml PBS. As a control, 150 µl of PBS without virus was injected into a mouse. At 24 hours post-injection, the animals were sacrificed and lacZ expression was detected by X-gal staining of tissues. A substantial number of blue cells was detected in all ten cyrosections of lung tissue of the mouse which received $6 \times 10^8$ pfu of Z4. No blue cells were detected in in lung tissue of control mice or in the examined cryosections from mice which received lower amounts of the virus. As is observed in vitro, expression of the exogenous gene is dose-dependent; the lower doses of virus did not yield detectable expression. Blue cells were not detected in sections of liver tissue of the mice which received the virus. In sum, these data indicate that injection of a non-mammalian DNA virus expressing an exogenous gene into a mammal can result in production of the exogenous gene product in vivo.

Other Embodiments

Non-mammalian viruses other than the above-described *Autographa californica* viruses can be used in the invention; such viruses are listed in Table 1. Nuclear polyhedrosis viruses, such as multiple nucleocapsid viruses (MNPV) or single nucleocapsid viruses (SNPV), are preferred. In particular, *Choristoneura fumiferana* MNPV, *Mamestra brassicae* MNPV, *Buzura suppressaria* nuclear polyhedrosis virus, *Orgyia pseudotsugata* MNPV, *Bombyx mori* SNPV, *Heliothis zea* SNPV, and *Trichoplusia ni* SNPV can be used.

Granulosis viruses (GV), such as the following viruses, are also included among those which can be used in the invention: *Cryptophlebia leucotreta* GV, *Plodia interpunctella* GV, *Trichoplusia ni* GV, *Pieris brassicae* GV, *Artogeia rapae* GV, and *Cydia pomonella* granulosis virus (CpGV). Also, non-occluded baculoviruses (NOB), such as *Heliothis zea* NOB and *Oryctes rhinoceros* virus can be used. Other insect (e.g., lepidopteran) and crustacean viruses may be used in the invention. Further examples of useful viruses include those which have infect fungi (e.g., *Strongwellsea magna*) and spiders. Viruses which are similar to baculoviruses have been isolated from mites, Crustacea (e.g., *Carcinus maenas*, *Callinectes sapidus*, the Yellow Head Baculovirus of penaeid shrimp, and *Penaeus monodon*-type baculovirus), and Coleoptera. Also useful in the invention is the *Lymantria dispar* baculovirus.

If desired, the virus can be engineered to facilitate targeting of the virus to certain cell types. For example, ligands which bind to cell surface receptors other than the ASGP-R can be expressed on the surface of the virion. Alternatively, the virus can be chemically modified to target the virus to a particular receptor.

If desired, the cell to be infected can first be stimulated to be mitotically active. In culture, agents such as chloroform can be used to this effect; in vivo, stimulation of liver cell division, for example, can be induced by partial hepatectomy (see, e.g., Wilson, et al., 1992, J. Biol. Chem. 267:11283–11489). Optionally, the virus genome can be engineered to carry a herpes simplex virus thymidine kinase gene; this would allow cells harboring the virus genome to be killed by gancicylovir. If desired, the virus could be engineered such that it is defective in growing on its natural non-mammalian host cell (e.g., insect cell). Such strains of viruses could provide added safety and be propagated on a complementing packaging line. For example, a defective baculovirus could be made in which an immediate early gene, such as IE1, has been deleted. This deletion can be made by targeted recombination in yeast or E. coli, and the defective virus can be replicated in insect cells in which the IE1 gene product is supplied in trans. If desired, the virus can be treated with neuraminidase to reveal additional terminal galactose residues prior to infection (see, e.g., Morell et al., 1971, J. Biol. Chem. 246:1461–1467).

I claim:

1. A method of expressing an exogenous gene in a mammalian cell, said method comprising:
   a) introducing into the cell a baculovirus, the genome of which comprises said exogenous gene operably linked to a mammalian-active promoter; and
   b) allowing said cell to live under conditions such that said exogenous gene is expressed.

2. The method of claim 1, wherein said baculovirus is a nuclear polyhedrosis virus.

3. The method of claim 2, wherein said nuclear polyhedrosis virus is an *Autographa californica* multiple nuclear polyhedrosis virus.

4. The method of claim 2, wherein said genome lacks a functional polyhedron gene.

5. The method of claim 1, wherein said baculovirus is in the occluded form.

6. The method of claim 1, wherein said baculovirus is in the budded form.

7. The method of claim 1, wherein said genome further comprises a promoter of a long-terminal repeat of a transposable element.

8. The method of claim 1, wherein said genome further comprises a promoter of a long-terminal repeat of a retrovirus.

9. The method of claim 8, wherein said retrovirus is Rous Sarcoma Virus.

10. The method of claim 1, wherein said genome further comprises an integrative terminal repeat of an adeno-associated virus.

11. The method of claim 10, wherein said genome further comprises an adeno-associated virus rep gene.

12. The method of claim 1, wherein said genome further comprises a cell-immortalizing sequence.

13. The method of claim 1, wherein said genome further comprises an origin of replication.

14. The method of claim 13, wherein said origin of replication comprises an Epstein Barr virus origin of replication.

15. The method of claim 1, wherein said genome further comprises a polyadenylation signal and an RNA splicing signal.

16. The method of claim 1, wherein said genome further comprises a cell-type-specific promoter.

17. The method of claim 16, wherein said cell-type-specific promoter comprises a liver cell-specific promoter.

18. The method of claim 17, wherein said liver cell-specific promoter comprises a promoter selected from the group consisting of the hepatitis B promoters, hepatitis A promoters, hepatitis C promoters, albumin promoters, $\alpha$-1-antitrypsin promoters, pyruvate kinase promoters, phosphenol pyruvate carboxykinase promoters, transferrin promoters, transthyretin promoters, $\alpha$-fetoprotein promoters, $\alpha$-fibrinogen promoters, and $\beta$-fibrinogen promoters.

19. The method of claim 18, wherein said genome comprises a hepatitis B promoter and further comprises a hepatitis B enhancer.

20. The method of claim 18, wherein said genome comprises an albumin promoter.

21. The method of claim 17, wherein said liver cell-specific promoter comprises a promoter of a gene selected from the group consisting of the low density lipoprotein receptor, $\alpha$2-macroglobulin, $\alpha$1-antichymotrypsin, $\alpha$2-HS glycoprotein, haptoglobulin, ceruloplasmin, plasminogen, complement proteins, C3 complement activator, $\beta$-lipoprotein, and $\alpha$1-acid glycoprotein.

22. The method of claim 1, wherein said cell is a hepatocyte.

23. The method of claim 22, wherein said hepatocyte is a primary hepatocyte.

24. The method of claim 22, wherein said hepatocyte is a HepG2 hepatocyte.

25. The method of claim 1, wherein said cell is a cell of the kidney cell line 293.

26. The method of claim 1, wherein said cell is a PC12 cell.

27. The method of claim 1, wherein said cell is selected from the group consisting of Sk-Hep-1 cells, NIH3T3 cells, HeLa cells, CHO/dhfr$^-$ cells, 293 cells, COS cells, and $C_2C_{12}$ cells.

28. The method of claim 1, wherein said cell is a primary cell.

29. The method of claim 28, wherein said baculovirus is introduced into said primary cell approximately 24 hours after plating of said primary cell.

30. The method of claim 1, wherein said baculovirus is introduced into said cell in vitro.

31. The method of claim 1 further comprising, allowing said cell to live on a substrate containing collagen.

32. The method of claim 31, wherein said collagen is rat tail Type I collagen.

33. The method of claim 1, wherein said cell is allowed to live under in vitro conditions.

34. The method of claim 1, wherein said mammalian cell is a human cell.

35. The method of claim 1, wherein said gene encodes a protein.

36. The method of claim 35, further comprising purifying said protein from said cell.

37. The method of claim 35, wherein said protein comprises a protein selected from the group consisting of carbamoyl synthetase I; ornithine transcarbamylase; arginosuccinate synthetase; arginosuccinate lyase; and arginase.

38. The method of claim 35, wherein said protein comprises a protein selected from the group consisting of fumarylacetoacetate hydrolase, phenylalanine hydroxylase, alpha-1 antitrypsin, glucose-6-phosphatase, low-density-lipoprotein receptor, and porphobilinogen deaminase, factor VIII, factor IX, cystathione $\beta$-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, $\beta$-glucosidase, pyruvate carboxylase, hepatic phosphorylase, phosphorylase kinase, glycine decarboxylase, H-protein, T-protein, Menkes disease protein, the product of Wilson's disease gene pWD, and CFTR.

39. The method of claim 1, wherein said exogenous gene is selected from the group consisting of lacZ genes, chloramphenicol acetyltransferase genes, alkaline phosphatase genes, luciferase genes, and green fluorescent protein genes.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AGCTGTCGAC TCGAGGTACC AGATCTCTAG A        31

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

AGCTTCTAGA GATCTGGTAC CTCGAGTCGA C        31

( 2 ) INFORMATION FOR SEQ ID NO:3:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GATCTGACCT AATAACTTCG TATAGCATAC ATTATACGAA GTTATATTAA GG        52

( 2 ) INFORMATION FOR SEQ ID NO:4:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GATCCCTTAA TATAACTTCG TATAATGTAT GCTATACGAA GTTATTAGGT CA        52